(12) United States Patent
Mochly-Rosen et al.

(10) Patent No.: US 10,131,691 B2
(45) Date of Patent: Nov. 20, 2018

(54) COMPOSITIONS AND METHODS FOR SPECIFIC REGULATION OF PYRUVATE DEHYDROGENASE KINASE

(71) Applicant: THE BOARD OF TRUSTEES OF THE LELAND STANFORD JUNIOR UNIVERSITY, Palo Alto, CA (US)

(72) Inventors: Daria Mochly-Rosen, Menlo Park, CA (US); Nir Qvit, Menlo Park, CA (US); Marie-Helene Disatnik Dziesietnik, Palo Alto, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 38 days.

(21) Appl. No.: 14/943,735

(22) Filed: Nov. 17, 2015

(65) Prior Publication Data

US 2016/0130302 A1 May 12, 2016

Related U.S. Application Data

(63) Continuation of application No. 14/238,449, filed as application No. PCT/US2012/050389 on Aug. 10, 2012, now Pat. No. 9,217,137.

(60) Provisional application No. 61/523,167, filed on Aug. 12, 2011.

(51) Int. Cl.
| | | |
|---|---|---|
| *C07K 7/08* | (2006.01) | |
| *C12N 9/12* | (2006.01) | |
| *C07K 7/06* | (2006.01) | |
| *A61K 38/00* | (2006.01) | |

(52) U.S. Cl.
CPC ............... *C07K 7/08* (2013.01); *C07K 7/06* (2013.01); *C12N 9/12* (2013.01); *C12Y 207/11002* (2013.01); *C12Y 207/11013* (2013.01); *A61K 38/00* (2013.01)

(58) Field of Classification Search
CPC .................................... C07K 7/08; C12N 9/12
See application file for complete search history.

(56) References Cited

U.S. PATENT DOCUMENTS

| | | | |
|---|---|---|---|
| 4,847,240 A | 7/1989 | Ryser et al. | |
| 5,747,647 A | 5/1998 | Stack et al. | |
| 5,804,604 A | 9/1998 | Frankel et al. | |
| 5,888,762 A | 3/1999 | Joliot et al. | |
| 6,593,292 B1 | 7/2003 | Rothbard et al. | |
| 7,166,575 B2* | 1/2007 | Quay | A61K 38/1709 514/21.3 |
| 7,393,835 B2 | 7/2008 | Mochly-Rosen | |
| 7,528,223 B2* | 5/2009 | Mattner | A61K 39/12 424/184.1 |
| 7,595,151 B2* | 9/2009 | Lu | A61K 38/07 435/287.1 |
| 7,863,245 B2* | 1/2011 | Quay | A61K 38/1709 514/5.2 |
| 7,910,111 B2* | 3/2011 | Lowenstein | C07K 14/705 424/204.1 |
| 2001/0044417 A1* | 11/2001 | Wolff | A61K 31/155 514/44 R |
| 2003/0045680 A1* | 3/2003 | Joyal | C07K 7/06 530/327 |
| 2003/0104622 A1 | 6/2003 | Robbins et al. | |
| 2003/0199677 A1 | 10/2003 | Avrameas et al. | |
| 2004/0037809 A1* | 2/2004 | Quay | A61K 9/0043 424/85.6 |
| 2004/0253239 A1* | 12/2004 | Jiang | C07K 14/475 424/145.1 |
| 2005/0164933 A1* | 7/2005 | Tymianski | C07K 14/47 514/1.2 |
| 2006/0099150 A1* | 5/2006 | Houston | A61K 38/1709 424/46 |
| 2006/0104964 A1* | 5/2006 | Jiang | C07K 14/475 424/93.21 |
| 2008/0119412 A1* | 5/2008 | Tymianski | C07K 14/47 514/1.2 |
| 2008/0153926 A1 | 6/2008 | Mochly-Rosen et al. | |
| 2009/0118158 A1* | 5/2009 | Quay | A61K 38/1709 514/1.1 |

FOREIGN PATENT DOCUMENTS

| | | |
|---|---|---|
| WO | WO 1999/038881 A1 | 8/1999 |
| WO | WO 2002/057413 A2 | 7/2002 |
| WO | WO 2004/011650 A2 | 2/2004 |
| WO | WO 2007/040711 A2 | 4/2007 |
| WO | WO 2010/11153 A2 | 9/2010 |

OTHER PUBLICATIONS

Umezawa et al., 2002, Translocation of a beta-Peptide Across Cell Membranes, J Am Chem Soc, 124(3): 368-369.*
Wu et al., 2010, A novel method for promoting heterologous protein expression in *Escherichia coli* by fusion with the HIV-1 TAT core domain, Amino Acids, 39: 811-820.*
Zaro et al., 2009, Nuclear Localization of Cell-Penetrating Peptides is Dependent on Endocytosis Rather Than Cytosolic Delivery in CHO cells, Mol Pharm, 6(2): 337-344.*
Vyas et al., 2008, TAT Opens the Door, Mol Ther, 16(4): 647 (5 pages).*
Cai et al., 2006, The kinetics and tissue distribution of protein transduction in mice, European Journal of Pharmaceutical Sciences, 27: 311-319.*

(Continued)

*Primary Examiner* — Amber D Steele
(74) *Attorney, Agent, or Firm* — McDermott Will & Emery LLP

(57) ABSTRACT

A peptide composition is provided which specifically inhibits the ability of δ-protein kinase C (δPKC) to phosphorylate pyruvate dehydrogenase kinase (PDK) under ischemic conditions. The peptide composition is useful for treating or reducing tissue damage resulting from ischemia and/or reperfusion.

5 Claims, 18 Drawing Sheets

Specification includes a Sequence Listing.

(56) References Cited

OTHER PUBLICATIONS

Cardarelli et al., 2008, Tuning the Transport Properties of HIV-1 Tat Arginie-Rich Motif in Living Cells, Traffic, 9: 528-539.*
Baker et al., "Marked differences between two isoforms of human pyruvate dehydrogenase kinase", J. Biol. Chem., vol. 275, No. 21, pp. 15773-15781 (2000).
Bates et al., "Intracoronary KAI-9803 as an adjunct to primary percutaneous coronary intervention for acute ST-segment elevation myocardial infarction", Circulation, vol. 117, No. 7, pp. 886-896 (2008).
Bright et al., "DeltaPKC mediates microcerebrovascular dysfunction in acute ischemia and in chronic hypertensive stress in vivo", Brain Res., vol. 1144, pp. 146-155 (2007).
Budas et al., "Aldehyde dehydrogenase 2 in cardiac protection: a new therapeutic target?", Trends Cardiovasc. Med., vol. 19, No. 5, pp. 158-164 (2009).
Budas et al., "Mitochondrial import of PKCepsilon is mediated by HSP90: a role in cardioprotection from ischaemia and reperfusion injury", Cardiovasc. Res., vol. 88, pp. 83-92 (2010).
Chen et al., "Opposing cardioprotective actions and parallel hypertrophic effects of delta PKC and epsilon PKC", PNAS USA, vol. 98, No. 20, pp. 11114-11119 (2001).
Chen et al., "Mitochondrial aldehyde dehydrogenase and cardiac diseases", Cardiovasc. Res., vol. 88, No. 1, pp. 51-57 (2010).
Churchill et al., "Reperfusion-induced translocation of deltaPKC to cardiac mitochondria events pyruvate dehydrogenase reactivation", Circ. Res., vol. 97, No. 1, pp. 78-85 (2005).
Churchill et al., "Rationally designed peptide regulators of protein kinase C", Trends Endocrinol. Metab., vol. 20, No. 1, pp. 25-33 (2009).
Connaughton et al., "Regulation of pyruvate dehydrogenase kinase isoform 4 (PDK4) gene expression by glucocorticoids and insulin", Mol. Cell Endocrinol., vol. 315, No. 1-2, pp. 159-167 (2010).
Green et al., "Structural and functional insights into the molecular mechanisms responsible for the regulation of pyruvate dehydrogenase kinase 2", J. Biol. Chem., vol. 283, vol. 283, pp. 15789-15798 (2008).
Gudi et al., "Diversity of the pyruvate-dehydrogenase kinase gene family in humans", J. Biol. Chem., vol. 270, No. 48, pp. 28989-28994 (1995).

Inagaki et al., "Inhibition of delta-protein kinase C protects against reperfusion injury of the ischemic heart in vivo", Circulation, vol. 108, No. 19, pp. 2304-2307 (2003).
International Search Report from PCT Patent Application No. PCT/US2012/050389 dated Oct. 12, 2012, Application now published as WO2013/025525 on Feb. 21, 2013.
Iwanami et al., "Striking the balance between PTEN and PDK1: it all depends on the cell context", Genes Dev., vol. 23, No. 15, pp. 1699-1704 (2009).
Kolobova et al., "Regulation of pyruvate dehydrogenase activity through phosphorylation at multiple sites", Biochem. J., vol. 358, Pt. 1, pp. 69-77 (2001).
Korotchkina and Patel, "Site specificity of four pyruvate dehydrogenase kinase isoenzymes toward the three phosphorylation sites of human pyruvate dehydrogenase", J. Biol. Chem., vol. 276, No. 40, pp. 37223-37229 (2001).
Lewandowski and White, "Pyruvate dehydrogenase influences postischemic heart function", Circulation, vol. 91, No. 7, pp. 2071-2079 (1995).
Patel et al., "Regulation of mammalian pyruvate dehydrogenase complex by phosphorylation: complexity of multiple phosphorylation sites and kinases", Exp. Mol. Med., vol. 33, No. 4, pp. 191-197 (2001).
Qi et al., "Aberrant mitochondrial fission in neurons induced by protein kinase C{delta} under oxidative stress conditions in vivo", Mol. Biol. Cell., vol. 22, No. 2, pp. 256-265 (2011).
Qvit et al., "A second generation peptide activator derived from the C2 domain of delta protein kinase C and regulates its function in the mitochondria", J. Peptide Sci., vol. 16, Suppl. 1, pp. 115-116, No. P215, Abstract No. 30, ID XP009164301 (2010).
Qvit et al., "Rational design of a novel peptide that selectively inhibits one delta PKC function", Biopolymers, vol. 96, No. 4, pp. 487, Abstract No. YI-P254, ID. XP009164300 (2011).
Qvit and Mochly-Rosen, "Highly Specific Modulators of Protein Kinase C Localization: Applications to Heart Failure", Drug Discov. Today Dis. Mech., vol. 7, No. 2, pp. e87-e93 (2010).
Schöder et al., "Regulation of pyruvate dehydrogenase activity and glucose metabolism in post-ischaemic myocardium", Biochem. Biophys. Acta, vol. 1406, No. 1, pp. 62-72 (1998).

* cited by examiner

```
HUMAN δPKC   KMKEALSTERGKTLVQ  46   Seq ID No:15
HUMAN PDK2   IYLKALSTDSVERLPV 402   Seq ID No:16
             ****^    *
```

PDK 3D Structure

| | | |
|---|---|---|
| Human δPKC | PFCAVKMKEALSTERGKTILVQKKPT 50 | SEQ ID NO:17 |
| Mouse δPKC | PFCAVKMKEALSTERGKTILVQKKPT 50 | SEQ ID NO:18 |
| Rat δPKC | PFCAVKMKEALTDRGKTILVQKKPT 50 | SEQ ID NO:19 |
| Chicken δPKC | PFCAIKMKEALTTERGKTILQRKPT 50 | SEQ ID NO:20 |
| Zebrafish δPKC | PFCAVKMKEALSTERGKTILVQKKPT 48 | SEQ ID NO:21 |
| | **********^*^**^^* | |

FIG. 1D

| | | |
|---|---|---|
| HUMAN PDK2 | FSMEGFGTDAVIYLKALSTDSV 368 | SEQ ID NO:22 |
| MOUSE PDK2 | FSMEGFGTDAVIYLKALSTDSV 368 | SEQ ID NO:23 |
| RAT PDK2 | FSMEGFGTDAVIYLKALSTDSV 368 | SEQ ID NO:24 |
| Chicken PDK | YSLEGYGTDAVIYIKALSTESI 383 | SEQ ID NO:25 |
| Zebrafish PDK2 | YPMEGYGTDAVIQLKALSTDSV 369 | SEQ ID NO:26 |
| Drosophila PDK | LSCEGFGTDAIIYLKALSDEAN 406 | SEQ ID NO:27 |
| | ^ ********** ^***^ ^^ | |

| | | |
|---|---|---|
| HUMAN PDK2 | FSMEGFGTDAVIYLKALSTDSV 368 | SEQ ID NO:22 |
| Worm PDK | VSMEGYGTDAMIFLKAIPVEAS 433 | SEQ ID NO:28 |
| YEAST PDK | QSLLGWGTDVYIKLKGPSKTAL 433 | SEQ ID NO:29 |
| | *^ * **** * ** | |

FIG. 1E

SEQ ID NO:30 Human εPKC  MVVFNGLLKIKICEAVSLKPTAWSLRHAVGPRPQTFLLDPYIALNVDDSR------IGQTATKQKTNSPAWH
                         *   ^   *^ *              ^* ***  ^ ^^                ^*   *    **
SEQ ID NO:31 Human δPKC  MA-PFLRISFNSYELGSLQ-------AEDEAN-----QPFCAVKMKEALSTERGKTLVQKKPTM---YPEWK
                         *^ *** ^^ *  *             ^    * ^ ^ *  ^**    *
SEQ ID NO:32 Human θPKC  MS-PFLRIGLSNFDCGSCQ-------SCQGEAV-----NPYCAVLVKEYVESENGQMYIQKKPTM---YPPWD εV1-2: EAVSLKPT
                         δV1-1: FNSYELGSLQ
                         θV1-1: SNFDCGSCQ
                         ΨPDK δV1-5: ALSTERGKTLVQ Human εPKC  DEFVTDVCNGRKIELAVFHDAPIGYDDFVANCTIQFEELLQNGSRHFEDWIDLEPEGKVVIIDLSGSSGEAPK
            *   ^   *^^ *    ^  ^        ^     ^  *******       ^ *    ^
Human δPKC  STFDAHIYEGRVIQIVLMRAAEEPMSEVTVGVSVLAERCKKNNGKAE-FWLDLQPQAKVLMSVQYFLEDVDCKQ
            ******* ^*^^^^^*                 *** ****  *    ^* ^ ** * *  *
Human θPKC  STFDAHINKGRVMQIIVKGKNVDLISETTVELYSLAERCRKNNGKTE-IWLELKPQGRMLMNARYFLEMSDTKD

ΨεRACK: HDAPIGYD
            ΨδRACK: MRAAEEPM
            ΨθRACK: KGKNVDLI

FIG. 1F

| | δV1-1 | ψδRACK | ψPDK |
|---|---|---|---|
| Translocation to Mito | → | ← | ← |
| Cardioprotective | Yes | No | Yes |

COMPOSITIONS AND METHODS FOR SPECIFIC REGULATION OF PYRUVATE DEHYDROGENASE KINASE

CROSS-REFERENCE TO RELATED APPLICATIONS

This application is a continuation application of U.S. application Ser. No. 14/238,449 filed Jul. 3, 2014, now issued as U.S. Pat. No. 9,217,137, which is a U.S. National Stage of International Patent Application No. PCT/US2012/050389, filed Aug. 10, 2012, which claims the benefit of priority to U.S. provisional application No. 61/523,167, filed Aug. 12, 2011, each of which is hereby incorporated by reference in its entirety.

STATEMENT REGARDING FEDERALLY SPONSORED RESEARCH

This invention was made with Government support under contract HL52141 awarded by the National Institutes of Health. The Government has certain rights in the invention.

CROSS-REFERENCE TO A SEQUENCE LISTING

A Sequence Listing is being submitted electronically via EFS in the form of a text file, created Jan. 12, 2016, and named 0915110594seqlist.txt 29444 bytes), the contents of which are incorporated herein by reference in their entirety.

TECHNICAL FIELD

This disclosure relates generally to peptide modulators of δPKC phosphorylation of pyruvate dehydrogenase kinase (PDK) and their methods of use for treatment of cardiac ischemia and reperfusion injury.

BACKGROUND

Protein-protein interactions are central to biological processes, determining the specificity of all cellular signaling events, and therefore represent an important class of drug targets. However, protein-protein interaction sites constitute large and flat interfaces (750-1500 Å) in each respective protein, rather than small hydrophobic, more 'drugable', pockets. Therefore, finding small-molecule inhibitors of protein-protein interaction has been proven to be a challenge (Arkin et al., 2004, Nat. Rev. Drug Discov., 3:301-317).

Members of the family of PKC isozymes are dependent on lipid-derived second messengers (as well as on calcium for some isozymes) that induce conformational changes, transforming the enzyme from an inactive to an active state. PKC activation is also associated with the translocation of the active enzymes to their partner proteins, RACKs (for receptor for activated C-Kinase), that facilitate the enzyme translocation (Ron et al., 1999, J. Biol. Chem., 274:27039-27046) to different sub-cellular sites (Mochly-Rosen, 1995, Science, 268:247-251). It was determined that the C2 domain in the regulatory region of PKC mediates at least some of the binding to their RACKs (Smith et al., 1992, Biochem. Biophys. Res. Commun., 188:1235-1240; Johnson et al., 1996, J. Biol. Chem., 271:24962-24966); unique sequences within the highly conserved C2 domain (e.g., βC2-4, δV1-1 and εV1-2 (Ron et al., 1995, J. Biol. Chem., 270:24180-24187; Chen et al., Proc. Natl. Acad. Sci. USA, 98:11114-11119; Gray et al., 1997, J. Biol. Chem., 272: 30945-30951) in each PKC isozyme are part of these interaction sites. Peptides representing these unique sequences (e.g., δV1-1) serve as competitive inhibitors, inhibiting the association of the corresponding isozyme with its RACK and therefore inhibiting all the functions of a given isozyme. On the other hand, inhibitory intra-molecular protein-protein interactions keep the enzyme in the inactive state. It has been shown that at least one such intra-molecular interaction occurs between the RACK-binding site in PKC and a sequence in the enzyme that is homologous to its RACK, termed pseudo RACK (ΨRACK) (Dorn et al., 1999, Proc. Natl., Acad. Sci., 96:12798-12803). A peptide corresponding to this WRACK site competes with the intra-molecular inhibitory interaction, thus serving as a selective activator of the corresponding isozyme.

δPKC regulating peptides are known to play a significant role in cardiac ischemia and reperfusion injury (i.e., heart attack-induced injury). It has been previously shown that treatment after the ischemic event with ΨδRACK, the δPKC-specific activator, increased δPKC-mediated cardiac injury whereas treatment with δV1-1, the δPKC specific inhibitor, blocked this injury (Chen et al., Proc. Natl. Acad. Sci. USA, 98:11114-11119) in a variety of animal models of myocardial infarction, including mice and rats (Chen et al., Proc. Natl. Acad. Sci. USA, 98:11114-11119), pigs (Inagaki et al, 2003, Circulation, 108:2304-2307), and possibly humans (Bates et al., 2008, Circulation, 117:886-896).

Numerous substrates for δPKC have been identified in a variety of cell types and they are found in different sub-cellular locations. Further, it has been demonstrated that ischemia and reperfusion induce the translocation of some of the activated δPKC into the mitochondria (Churchill et al., 2005, Cir. Res., 97:78-85), leading to increased phosphorylation of the intra-mitochondrial enzyme, pyruvate dehydrogenase kinase (PDK). Phosphorylation of pyruvated dehydrogenase (PDH) by PDK results in decreased activity of PDH, thereby leading to the inhibition of the TCA cycle and ATP regeneration. Studies have suggested that cardiac efficiency and recovery of contractile function in postischemic hearts can be improved by pharmacological stimulation of PDH (Lewandowski et al., 1995, Circulation, 91:2017-2079; Schoder et al., 1998, Biochim Biophys. Acta., 1406:62-72). However, it was not clear whether phosphorylation of PDK alone by δPKC is responsible for resulting cardiac injury following ischemia and reperfusion (I/R). It is possible that any of the other δPKC substrates alone or together with PDK may contribute to or be critical for this injury.

To determine the importance of δPKC-mediated PDK phosphorylation for cardiac injury by I/R, a peptide inhibitor was designed that selectively inhibits PDK phosphorylation by δPKC without affecting the phosphorylation of other substrates of this isozyme. Since selective inhibitors and activators for PDK itself are not available, such a separation-of-function inhibitor of δPKC provides both an important tool to address the above question as well as the basis for a therapeutic composition for the treatment at least of tissue injury by ischemia and reperfusion.

BRIEF SUMMARY

In a first aspect, a modulatory peptide is provided, wherein the peptide comprises a core amino acid sequence, wherein the core sequence is 5 amino acid residues in length, and wherein the core sequence is at least 60% identical to the sequence ALSTE (SEQ ID NO:1).

In one embodiment, the core sequence is 6 amino acid residues in length, and the core sequence is at least 60% identical to the sequence ALSTER (SEQ ID NO:2).

In one embodiment, the modulatory peptide comprises of 5-20 amino acid residues. In another embodiment, the modulatory peptide comprises of 5-15 amino acids, 5-10 amino acids, 6-15 amino acids, 6-10 amino acids, or 6-8 amino acids. In still another embodiment, the modulatory peptide comprises 5 amino acids, 6 amino acids, 7 amino acids, 8 amino acids, 9 amino acids, 10 amino acids, 11 amino acids, 12 amino acids, 13 amino acids, 14 amino acids, or 15 amino acids.

In one embodiment, the modulatory peptide is at least about 60% identical to a contiguous sequence of equal length derived from pyruvate dehydrogenase kinase (PDK). In another embodiment, the modulatory peptide is at least about 70%, 80%, 85%, 90%, 95%, 96%, 97%, 98% or 99% identical to a contiguous sequence of equal length derived from PDK.

In one embodiment, the modulatory peptide is not ALSTERGKTLV (SEQ ID NO:43), ALSTDRGKTLV (SEQ ID NO:44), ALTTDRGKTLV (SEQ ID NO:45), ALTTDRGRTLV (SEQ ID NO:46), ALTTDRGKSLV (SEQ ID NO:47), ALTSDRGKTLV (SEQ ID NO:48), ALTTDRP-KTLV (SEQ ID NO:49), ALTTDKGKTL (SEQ ID NO:50), and/or ALTTDRGKLV (SEQ ID NO:51).

In one embodiment, the modulatory peptide inhibits phosphorylation of PDK by δ-Protein Kinase C (δPKC). In another embodiment, the modulatory peptide specifically inhibits phosphorylation of PDK by δPKC.

In one embodiment, the modulatory peptide further comprises a sulfur-containing residue. In another embodiment, the sulfur-containing residue is cysteine. In still another embodiment, the sulfur-containing residue is a cysteine analog.

In one embodiment, the sulfur-containing residue is located at the N-terminus and/or the C-terminus of the modulatory peptide. In another embodiment, the sulfur-containing residue is an internal residue.

In one embodiment, the modulatory peptide is linked to a carrier peptide. In one embodiment, the modulatory peptide is linked to a carrier peptide by a disulfide bond. In another embodiment, the modulatory peptide is linked to the carrier peptide by a peptide bond, wherein the modulatory peptide and the carrier form a single modulatory fusion peptide.

In one embodiment, the carrier peptide is a TAT peptide. In another embodiment the carrier peptide is $TAT_{47-57}$ (SEQ ID NO:33). In yet another embodiment, the carrier peptide further comprises a sulfur-containing residue. In still another embodiment, the sulfur-containing residue is cysteine. In another embodiment, the sulfur-containing residue is a cysteine analog. In still another embodiment, the carrier peptide further comprises a cysteine residue attached via a peptide bond to its C-terminus (SEQ ID NO:52) or N-terminus (SEQ ID NO:53). In yet another embodiment, a cysteine residue is present at any alternative is the presence of a cysteine residue at any position within SEQ ID NO:33.

In a second aspect, a method for modulating the activity of PDK is provided.

In a third aspect, a method for treating a subject comprising administration of a selective δPKC-modulatory composition is provided.

In one embodiment, the method comprises administering to a subject in need thereof, a ΨPDK modulatory peptide.

In one embodiment, the subject is suffering from cardiovascular disease, cardiac ischemia, cardiac ischemia/reperfusion injury, myocardial infarction, chronic stable angina, or acute coronary syndrome. In another embodiment, the subject is undergoing or has undergone a heart transplant.

These and other objects and features of the invention will become more fully apparent when read in conjunction with the following detailed description.

BRIEF DESCRIPTION OF THE FIGURES

FIG. 1D illustrates an amino acid sequence alignment of a partial sequence of δPKC from various species.

FIG. 1E illustrates an amino acid sequence alignment of a partial sequence of PDK2 from various species FIG. 1F shows an amino acid sequence alignment of the ε-, δ-, and θ-PKC C2 domains, also illustrating isozyme-specific inhibitors (top) and activators (bottom) for each isozyme.

DETAILED DESCRIPTION

Figure 1A:
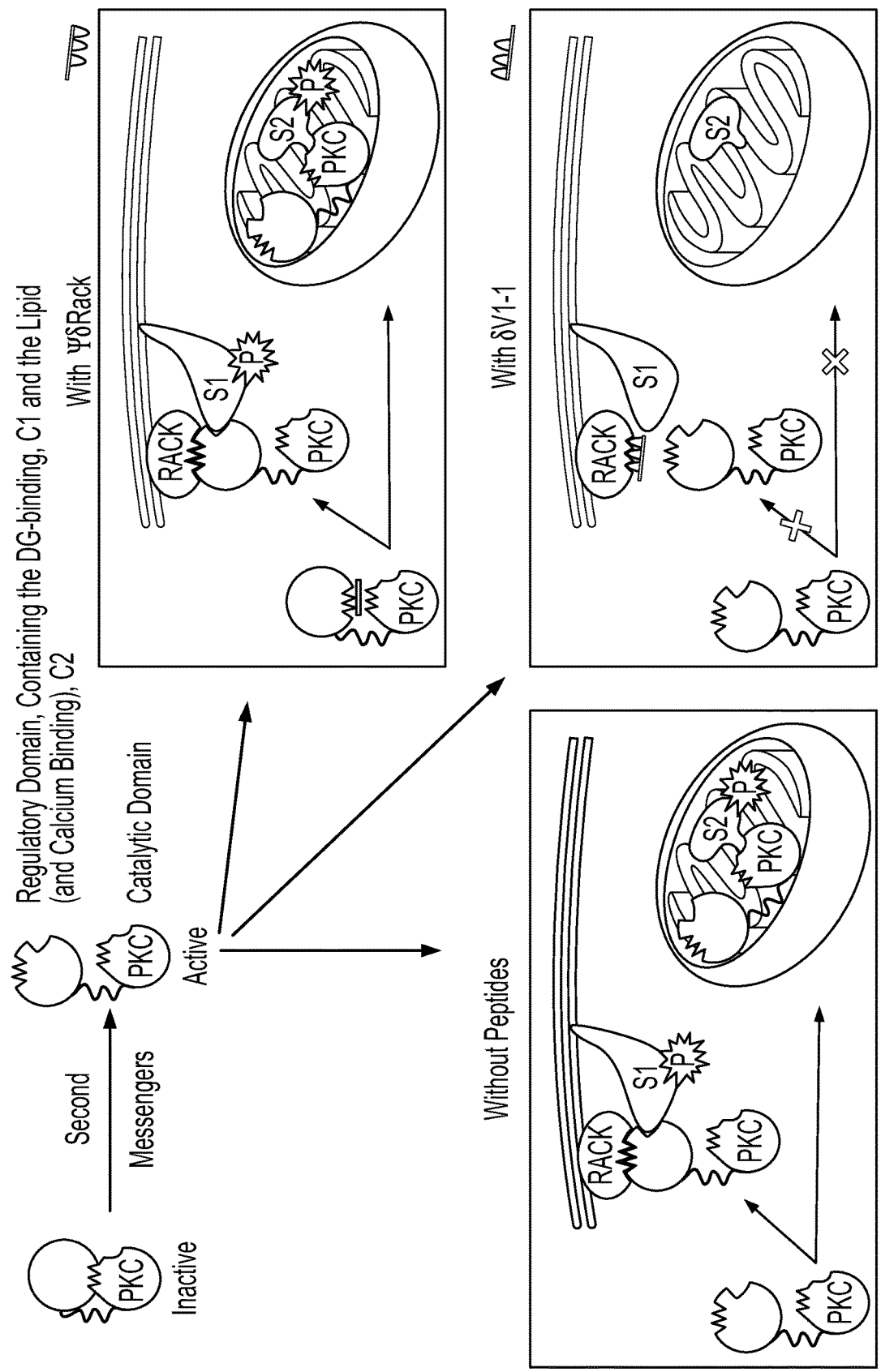
FIG. 1A is a schematic showing mechanisms involving regulation of PKC translocation and activity in the presence or absence of second messengers or modulator peptides.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

The practice of the present disclosure will employ, unless otherwise indicated, conventional methods of chemistry, biochemistry, and pharmacology, within the skill of the art. Such techniques are explained fully in the literature. See, e.g.; A. L. Lehninger, *Biochemistry* (Worth Publishers, Inc., current addition); Morrison and Boyd, *Organic Chemistry* (Allyn and Bacon, Inc., current addition); J. March, *Advanced Organic Chemistry* (McGraw Hill, current addition); *Remington: The Science and Practice of Pharmacy*, A. Gennaro, Ed., 20$^{th}$ Ed.; *Goodman & Gilman The Pharmacological Basis of Therapeutics*, J. Griffith Hardman, L. L. Limbird, A. Gilman, 10$^{th}$ Ed.

Where a range of values is provided, it is intended that each intervening value between the upper and lower limit of that range and any other stated or intervening value in that stated range is encompassed within the disclosure. For example, if a range of 1% to 8% is stated, it is intended that 2%, 3%, 4%, 5%, 6%, and 7% are also explicitly disclosed, as well as the range of values greater than or equal to 1% and the range of values less than or equal to 8%.

I. Definitions

It must be noted that as used herein and in the appended claims, the singular forms "a", "an", and "the" include plural reference unless the context clearly dictates otherwise.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the methodologies which are reported in the publications which might be used in connection with the invention.

The term "substantially purified", as used herein, refers to nucleic or amino acid sequences that are removed from their natural environment, isolated or separated, and are at least 60% free, preferably 75% free, more preferably 90% free, and most preferably 95% free from other components with which they are naturally associated or associated with by virtue of the purification process.

"Peptide" and "polypeptide" are used interchangeably herein and refer to a compound made up of a chain of amino acid residues linked by peptide bonds. Unless otherwise indicated, the sequence for peptides is given in the order from the amino terminus to the carboxyl terminus. A "substitution", as used herein, refers to the replacement of one or more amino acids by different amino acids, respectively. "Conservative amino acid substitutions" are substitutions which do not result in a significant change in the activity or tertiary structure of a selected polypeptide. Conservative amino acid substitutions may be made in the amino acid sequences to obtain derivatives of the peptides that may advantageously be utilized in the present invention. Conservative amino acid substitutions, as known in the art and as referred to herein, involve substituting amino acids in a protein with amino acids having similar side chains in terms of, for example, structure, size and/or chemical properties. For example, the amino acids within each of the following groups may be interchanged with other amino acids in the same group as follows: amino acids having aliphatic side chains, including glycine, alanine, valine, leucine and isoleucine; amino acids having non-aromatic, hydroxyl-containing side chains, such as serine and threonine; amino acids having acidic side chains, such as aspartic acid and glutamic acid; amino acids having amide side chains, including glutamine and asparagine; basic amino acids, including lysine, arginine and histidine; amino acids having aromatic ring side chains, including phenylalanine, tyrosine and tryptophan; and amino acids having sulfur-containing side chains, including cysteine and methionine. Additionally, aspartic acid, glutamic acid and their amides, are also considered interchangeable herein.

An "insertion" or "addition," as used herein, refers to a change in an amino acid sequence resulting in the addition of one or more amino acid residues, as compared to the naturally occurring molecule.

A "deletion," as used herein, refers to a change in the amino acid sequence and results in the absence of one or more amino acid residues.

A "variant" of a first amino acid sequence refers to a second amino acid sequence that has one or more amino acid substitutions or deletions, relative to the first amino acid sequence.

A "modification" of an amino acid sequence or a "modified" amino acid sequence refers to an amino acid sequence that results from the addition of one or more amino acid residues, to either the N-terminus or the C-terminus of the sequence. A "modification" may also refer to a chemical modification to one or more amino acids within the peptide sequence, such as incorporation of an amino acid analog. The amino acid analog may be a naturally occurring analog or synthetic.

The term "modulate" or "regulate," as used herein, refers to a change in the activity of pyruvate dehydrogenase kinase (PDK). For example, modulation or regulation may cause an increase or a decrease in protein activity, binding characteristics, or any other biological, functional or immunological properties of the PDK.

Reference herein to an "amino acid sequence having 'x' percent identity" with another sequence intends that the sequences have the specified percent identity, 'x', determined as set forth below, and share a common functional activity. To determine the percent identity of two amino acid sequences, the sequences are aligned for optimal comparison purposes (e.g., gaps can be introduced in one or both of a first and a second amino acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 75%, 80%, 85%, 90%, or 95% of the length of the reference sequence. For the relatively short peptide sequences described herein, percent identity is taken as the number of like residues between the first and second sequence relative to the total number of residues in the longer of the first and second sequences. The comparison of sequences and determination of percent identity between two sequences can also be accomplished using a mathematical algorithm. The percent identity between two amino acid sequences can be determined using the Needleman and Wunsch (J. Mol. Biol., 48:444-453 (1970)) algorithm which has been incorporated into the GAP program in the GCG software package (available at the GCG website), using either a Blosum 62 matrix or a PAM250 matrix, and a gap weight of 16, 14, 12, 10, 8, 6, or 4 and a length weight of 1, 2, 3, 4, 5, or 6. The percent identity between two amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. Protein sequences can further be used as a "query sequence" to perform a search against public databases; for example, BLAST protein searches can be performed with the XBLAST program, score=50, wordlength=3. See the NCBI website.

"Ischemia" is defined as an insufficient supply of blood to a specific organ or tissue. A consequence of decreased blood supply is an inadequate supply of oxygen and nutrients to the organ or tissue (hypoxia). Prolonged hypoxia may result in injury to the affected organ or tissue.

"Anoxia" refers to a virtually complete absence of oxygen in the organ or tissue, which, if prolonged, may result in death of the organ or tissue.

"Hypoxic condition" is defined as a condition under which a particular organ or tissue receives an inadequate supply of oxygen.

"Anoxic condition" refers to a condition under which the supply of oxygen to a particular organ or tissue is cut off.

"Ischemic injury" refers to cellular and/or molecular damage to an organ or tissue as a result of a period of ischemia.

"Reperfusion" refers to return of fluid flow into a tissue after a period of no-flow or reduced flow. For example, in reperfusion of the heart, fluid or blood returns to the heart through a supply line, such as the coronary arteries in vivo, after removal of an occlusion to the fluid or blood supply.

The term "pyruvate dehydrogenase kinase" or "PDK" refers to any one of 4 known PDK isozymes. Four known human isozymes include PDK1 (GenBank Accession No. NP_002601; SEQ ID NO:11), PDK2 (GenBank Accession No. NP_002602; SEQ ID NO:12), PDK3 (GenBank Accession No. NP_001135858; SEQ ID NO:13), and PDK4 (GenBank Accession No. NP_002603; SEQ ID NO:14). PDK may also refer to PDK isozymes from other organisms, including but not limited to, rat, mouse, and chicken. In some embodiments, PDK may refer to a protein which has a sequence which is at least 60%, 65%, 70%, 75%, 80%, 85%, 90% or 95% identical to the human PDK1, PDK2, PDK3, or PDK4 protein sequence.

"Specific" or "specificity" refers to the selective modulation by a ΨPDK peptide or ΨPDK peptide composition, of δPKC phosphorylation by δPKC. A ΨPDK peptide can be tested for its specificity of modulation (inhibiting or activating) by comparing the amount of phosphorylation of PDK by δPKC to the amount of phosphorylation of other known δPKC phosphorylation substrates in the presence or absence of the ΨPDK peptide or ΨPDK peptide composition. In one embodiment, the addition of a specific ΨPDK peptide inhibitor to a phosphorylation assay to measure phosphorylation of PDK by δPKC in the presence and absence of the ΨPDK peptide results in a decrease in phosphorylation of PDK by δPKC. In this embodiment, the decrease in phosphorylation of PDK by δPKC at least a 1.5-fold, at least a 2-fold, at least a 3-fold, at least a 4-fold, at least a 5-fold, at least a 10-fold, at least a 20-fold, at least a 50-fold, or at least a 100-fold greater than decrease in phosphorylation by δPKC of a known δPKC phosphorylation substrate that is not PDK.

II. Rational Design of Pyruvate Dehydrogenase Kinase (PDK) Modulator Peptides

It has been previously shown that treatment of a cardiac ischemia and reperfusion injury (i.e., heart attack-induced injury) with ΨδRACK, a δPKC-specific activator, increased δPKC-mediated cardiac injury, whereas treatment with δV1-1, a δPKC-specific inhibitor peptide, blocked this injury (Chen et al., 2001, Proc. Natl. Acad. Sci. U.S.A., 98:11114-11119) in a variety of animal models of myocardial infarction, including mice and rats (Chen et al., 2001, Proc. Natl. Acad. Sci. U.S.A., 98:11114-11119), pigs (Inagaki et al., 2003, Circulation, 108:2304-2307), and possibly humans (Bates et al., 2008, Circulation, 117:886-896).

Numerous substrates for δPKC have been identified in a variety of cell types and they are found in different subcellular locations. These include, but are not necessarily limited to, myristoylated alanine-rich C-kinase substrate (MARCKS) (Disatnik et al., 2002, J. Cell. Sci., 115:2151-2163; Myat et al., 1997, Curr. Biol. 7:611-614), occludin (Qi et al., 2008, J. Clin. Inv., 118:173-182), and several ion channels (Barman et al., 2004, Am. J. Physiol. Lung Cell. Mol. Physiol., 186:L1275-L1281) that are found at the plasma membrane; c-Abl is on the endoplasmic reticulum (Qi et al., 2008, J. Cell Sci., 121:804-813); dynamin-related protein 1 (Drp-1) on the mitochondria (Qi et al., 2010, Mol. Biol. Cell., 22:256-265); and pyruvate kinase and a heat shock protein (HSP27) are in the cytosol (Siwko et al., 2007, Int. J. Biochem. Cell Biol., 39:978-987).

Below is described work related to the identification and characterization of a peptide modulator which specifically inhibits phosphorylation of PDK by δPKC after exposure of tissue to ischemia/reperfusion. This highly selective peptide is effective in reducing tissue damage normally observed after an ischemic/reperfusion event, thereby giving rise to a new therapy for the treatment and/or prevention of ichemic damage.

A rational design approach was used to identify a specific inhibitor of a single phosphorylation function of δPKC—the phosphorylation of PDK. This rational approach has been used previously to identify peptides that selectively inhibit PKC activity (Chen et al., Proc. Natl. Acad. Sci. U.S.A., 98:11114-11119; Brandman et al., 2007, J. Biol. Chem., 282:4113-4123) by interfering with PKC anchoring to its binding protein RACK (such as εV1-1 and δV1-1; FIG. 1a, e) (Johnson et al., 1996, J. Biol. Chem., 24962-24966; Dorn et al., 1999, Proc. Natl. Acad. Sci. U.S.A., 96:12798-12803;

Brandman et al., 2007, J. Biol. Chem., 282:4113-4123). Additionally, peptides that interfere with the auto-inhibitory interactions and thus act as activators of the corresponding isozyme (e.g., ΨεRACK and ΨδRACK) have been identified (Chen et al., Proc. Natl. Acad. Sci. U.S.A., 98:11114-11119; Ron et al., 1995, Proc. Natl. Acad. Sci. U.S.A., 92:492-496).

This inhibitor was then used to show that δPKC-mediated phosphorylation of PDK is required for δPKC-dependent cardiac injury following an ischemic event. This peptide inhibitor, referred to herein as ΨPDK, inhibited δPKC-mediated phosphorylation of PDK, but not the phosphorylation of other δPKC substrates, such as MARCKS or Drp1. Its specificity for δPKC was also evident by the absence of ΨPDK effect in cells lacking δPKC.

ΨPDK peptide represents a short sequence of similarity between PDK2 (ALSTD; SEQ ID NO:5), a direct substrate of δPKC, and δPKC (ALSTE; SEQ ID NO:1). Like the ΨPDK site, ALSTE, these peptides are all derived from the C2 domain. However, the action of ΨPDK is different.

The term "ΨPDK" refers to a peptide sequence which selectively inhibits phosphorylation of PDK by δPKC. In other words, a composition comprising a ΨPDK peptide will reduce phosphorylation of PDK by δPKC but will not affect phosphorylation of any other substrates known to be phosphorylated by δPKC (and described above). It is understood that ΨPDK will encompass a peptide whose effect on δPKC phosphorylation of such substrates (which are not PDK) is merely less than the effect of that ΨPDK peptide on the phosphorylation of PDK by δPKC under equivalent assay conditions. A "less" effect may encompass a decrease of 5%-20%, 10%-50%, 30%-50%, 40%-60%, 50%-80%, 70%-90%, 80%-95%, or 90-99% in phosphorylation by δPKC. Alternatively, this "less" effect encompasses at least a 50%, 60%, 70%, 80%, 90%, 95%, 97%, 98% or 99% decrease in phosphorylation by δPKC.

ΨPDK comprises a core amino acid sequence which is similar to the selective modulator peptide which was identified as described herein. This core amino acid sequence is at least 60% identical to the PDK2 sequence, ALSTE (SEQ ID NO:1). However, a peptide which can selectively inhibit phosphorylation of PDK by δPKC may be significantly longer than this core sequence of 5 amino acid residues. For example, a ΨPDK modulator peptide may be 5-20 amino acids in length, or 6-15 amino acids in length. In some embodiments, the additional amino acids, which may be N-terminal, C-terminal or both N-terminal and C-terminal to the core sequence are derived from a PDK sequence. Accordingly, the entire length of the ΨPDK modulator peptide will be at least 60%, 70%, 80%, 85%, 90%, 95%, or 99% identical to a same length of sequence within the PDK protein for which the ΨPDK modulator peptide is effective. Although the peptides are described primarily with reference to amino acid sequences from *Homo sapiens*, it is understood that the peptides are not limited to the specific amino acid sequences set forth herein.

It will be appreciated that the ΨPDK peptides can be used in native form or modified by conjugation to a carrier, such as those described below. Alternatively, one or two amino acids from the sequences can be substituted or deleted and exemplary modifications and derivatives and fragments for each peptide are given below. In some embodiments, the ΨPDK peptide is AISTER (SEQ ID NO:6), AVSTER (SEQ ID NO:7), ALTTER (SEQ ID NO:8), ATSSER (SEQ ID NO:9) or ALSTDR (SEQ ID NO:10).

III. Modulatory ΨPDK Peptide Compositions Comprising a Carrier Moiety

The modulatory ΨPDK peptide useful in inhibiting δPKC-specific PDK phosphorylation can be attached or linked to a peptide moiety which facilitates transfer of the modulatory peptide composition across a cell membrane. This peptide carrier may be any one of a number of peptide carriers known in the art for facilitating transfer across cell membranes, including Tat, the *Drosophila* Antennapedia protein, a polycationic peptide such as polyarginine (e.g., heptaarginine) or polylysine, penetratin, Tat, VT5, MAP, Transportan, Transportan-10, pVEC, pISL, Pep-1, and Mouse PrPC (1-28) (see Lundberg et al., 2003, J. Mol. Recognit., 16:227-233, U.S. Pat. Pub. Nos. 2003/0104622 and 2003/0199677). In a preferred embodiment, the carrier peptide is Tat-derived transport polypeptide (U.S. Pat. Nos. 5,747,647 and 5,804,604; Vives, et al. J. Biol. Chem., 272:16010-16017 (1997)), polyarginine (U.S. Pat. Nos. 4,847,240 and 6,593,292; Mitchell et al., 2000; Rothbard et al., 2000) or Antennapedia peptide (U.S. Pat. No. 5,888,762). The disclosures of these references are incorporated herein in their entirety.

The modulatory peptide may be linked to the carrier peptide by a disulfide bond. In some embodiments, the disulfide bond is formed between a two cysteines, two cysteine analogs or a cysteine and a cysteine analog. In this embodiment, both the modulatory peptide and the carrier peptide contain at least one cysteine or cysteine analog. The cysteine residue or analog may be present as the N-terminal or C-terminal residue of the peptide or as an internal residue of the modulatory peptide and of the carrier peptide. The disulfide linkage is then formed between the sulfur residues on each of the cysteine residues or analogs. Thus, the disulfide linkage may form between, for example, the N-terminus of the modulatory peptide and the N-terminus of the carrier peptide, the C-terminus of the modulatory peptide and the C-terminus of the carrier peptide, the N-terminus of the modulatory peptide and the C-terminus of the carrier peptide, the C-terminus of the modulatory peptide and the N-terminus of the carrier peptide, or any other such combination including at any internal position within the modulatory peptide and/or the carrier peptide.

The modulatory peptide can alternatively be part of a fusion protein. Typically, to form a fusion protein, the peptide is bound to another peptide by a bond other than a Cys-Cys bond. An amide bond from the C-terminal of one peptide to the N-terminal of the other is exemplary of a bond in a fusion protein. This embodiment encompasses the presence of a peptide bond between and linking the modulatory and carrier peptides to form a single linear peptide composition comprising both the modulatory peptide and the carrier peptide. The modulatory peptide may be N-terminal to the carrier peptide, or the carrier peptide may be N-terminal to the modulatory peptide.

A short linker peptide may be present between the modulatory peptide and the carrier peptide within the single linear peptide composition. The linker peptide may comprise 2 to 15 amino acid. Alternatively, the linker peptide may comprise 2 to 10 amino acids, 3 to 10 amino acids, 4 to 10 amino acids, 2 to 8 amino acids, 3 to 7 amino acids, or 4 to 6 amino acids. The linker peptide may comprise 2, 3, 4, 5, 6, 7, 8, 9, 10, 11, 12, 13, 14, or 15 amino acids. In some embodiments, the linker peptide comprises 1, 2, 3, 4, or 5 glycine residues. In other embodiments, the linker peptide comprises 1, 2, 3, 4 or 5 alanine residues. In still other embodiments, the linker peptide comprises at least 1 serine residue. In a preferred embodiment, the linker is Gly-Ser-Gly. It is understood that the linker peptide may comprise any amino acid or amino acid analog. The single linear peptide composition may alternative have a single amino acid present between the modulatory peptide and the carrier peptide.

IV. ΨPDK Mode of Action

Figure 8:
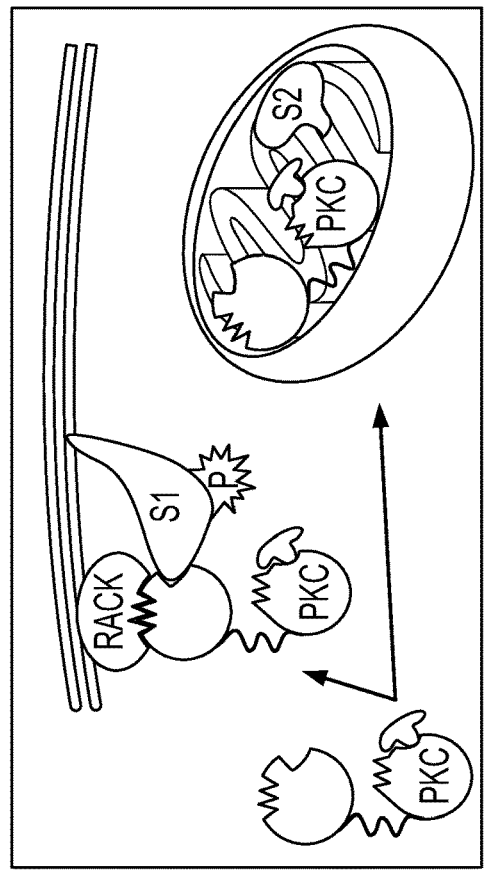
FIG. 8 is a schematic summarizing effects of a ΨPDK peptide on δPKC translocation and activity. S1 indicates MARCKS. S2 indicates PDK.
Figure 8:
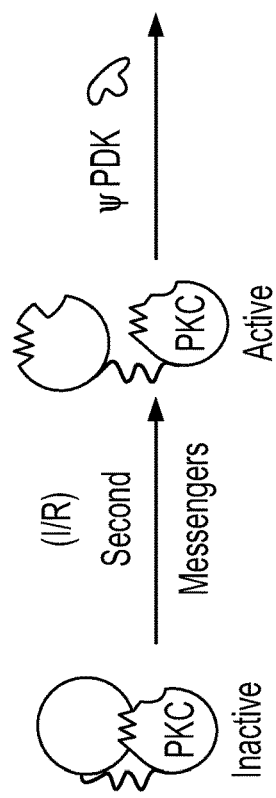

FIG. 8 provides a scheme summarizing the mode of action of ΨPDK. ΨPDK increases phosphorylation of substrates in the cytosol (S1, boxed in green on the left), but it inhibits the phosphorylation of PDK (S2, boxed in red on the right). The inhibitory effect of ΨPDK differs from δV1-1, which inhibits of δPKC phosphorylation of all substrates in any subcellular compartment (see FIG. 1A middle panel). ΨPDK also differs from ΨδRACK (FIG. 1A, right panel), which increases the phosphorylation of all the δPKC substrates. Therefore, ΨPDK is the first δPKC-specific peptide modulator which it distinguishes between δPKC function related to PDK regulation of mitochondrial function without inhibiting other δPKC-mediated functions. Importantly, ΨPDK demonstrates that δPKC-mediated phosphorylation of PDK could be the primary or only phosphorylation event that is required for δPKC-dependent cardiac injury following an ischemic event.

Many mitochondrial proteins have a mitochondrial targeting signal (MTS) composed of 20-50 amino acids at their N-termini that are recognized by the mitochondrial import system. Because δPKC does not contain such a mitochondrial targeting sequence, experiments were done to confirm that ΨPDK actually induced δPKC entry into mitochondria. δPKC-associated with the mitochondrial fractions was resistant to proteinase K digestion (FIG. 4C), indicating that δPKC does enter the mitochondria. However, the mechanism of δPKC import into the mitochondria remains to be identified.

The mitochondrial enzyme pyruvate dehydrogenase (PDH), is the key regulator of glycolytic contributions to aerobic respiration in the heart, as it converts pyruvate derived from glycolysis to acetyl-CoA for entry into the Krebs cycle. Part of the enzyme activity is regulated by phosphorylation- and dephosphorylation-dependent inhibition and activation, respectively (Patel et al., 2001, Exp. Mol. Med., 33:191-197). The enzyme that catalyses the phosphorylation of PDH and modulates its activity is PDK. There is evidence that PDH regulates recovery of contractile function of the heart after ischemia (Lewandowski et al., 1995, Circulation, 91:2071-2079; Stanley et al., 1996, J. Mol. Cell. Cardiol., 28:905-914). Here, it is shown that I/R-induced increased PDK phosphorylation, which is associated with increased PDH phosphorylation, is blocked in the presence of ΨPDK (FIG. 5). The same results are obtained when the δPKC-specific inhibitor, δV1-1, is added at reperfusion (FIG. 5). Since $TAT_{47-57}$ peptide, the peptide carrier in this study, has been shown to cross the mitochondrial membrane (Rayapureddi et al., 2010, Biochemistry, 49:9470-9479; Gaizo et al., 2003, Mol. Genet. Metab., 80:170-180), it is possible that the ΨPDK-TAT conjugate crossed the mitochondrial membrane and blocked the PDK/δPKC interaction inside the mitochondria. This effect may be in addition to the interaction of ΨPDK with δPKC in the cytosolic fraction, which leads to δPKC translocation and increased MARCKS phosphorylation (FIGS. 2, 5). In addition, it is shown herein that ΨPDK decreases PDK phosphorylation in vitro, without affecting the phosphorylation of Drp1, another δPKC-specific substrate that binds to δPKC upon translocation to the mitochondria to mediate mitochondrial fission (Qi et al, 2010, Mol. Biol. Cell., 22:256-265). Since it was shown that ΨPDK does not block the interaction of δPKC with its cytosolic substrate Drp1, or with MARCKS, located at the plasma membrane, it is concluded that the effect of ΨPDK is specific for the phosphorylation of PDK by δPKC.

Kinase modulators are very important for basic research as well as drugs. Numerous kinase modulators have been developed earlier. Most of these regulators are small molecules many with broad activity and other with higher selectivity (Karaman et al., 2008, Nat. Biotech., 26:127-132). To our knowledge, however, this is the first time that a modulator peptide specific for a single signaling molecule is reported. Our work demonstrates such specific regulators can be rationally designed and that these peptides provide missing tools to determine the role of one of several cellular functions of, for example, a given PKC isozyme. This approach is likely applicable to other signaling proteins, allowing the generation of separation-of function regulators of other protein-protein interactions.

V. Methods of Use

The modulatory peptides and peptide compositions described herein may be administered to a subject in need thereof to prevent or reduce organ, tissue, and or cell damage due to ischemia and resulting hypoxia. Such peptides are useful for slowing or inhibiting the progression of heart failure following ischemia, prolonging survival, reducing fractional shortening, reducing left ventricular weight to body weight ratio, reducing fibrosis, causing the EKG/ECG of a subject to more closely resemble that of a healthy animal, and/or combinations thereof. The peptides may be of particular value in protecting a heart from ischemic damage during a transplantation procedure. Accordingly, the peptides and peptide compositions described in here are useful for the treatment of a subject suffering from, for example, cardiovascular disease, cardiac ischemia, cardiac ischemia/reperfusion injury, myocardial infarction, chronic stable angina, or acute coronary syndrome, or is undergoing or has undergone a heart transplant.

In certain embodiments, there is provided a method of treating an individual at risk or with an established cardiovascular disorder. Such a method comprises the step of administering to the individual a pharmacologically effective amount of a ΨPDK peptide composition that reduces damage of or injury to cardiac tissue. "An effective amount" or "pharmacologically effective amount" refers to the amount of compound that is required to confer therapeutic effect on the treated subject, e.g., reduced reperfusion injury, etc. Effective doses will also vary, as recognized by those skilled in the art, depending on the route of administration, the excipient usage, and the optional co-usage with other therapeutic treatments. In still yet another embodiment, there is a method of protecting the heart from cardiovascular disease. Such a method comprises administering a ΨPDK peptide composition wherein the administering results in a reduction in myocardial infarct size, improves cardiac hemodynamic performance, improves heart failure symptoms, reduces apoptotic effect of cardiotoxic drug or combinations thereof, as compared to said results in the absence of administering a ΨPDK peptide composition or administering a control peptide composition. The reducing can refer to a 10%, 20%, 30%, 40%, 50%, 60%, 70%, 80%, 90%, or 100% decrease, or any value or range there between, in the amount of injury due to ischemia and/or reperfusion, including but not limited to infarct size.

In certain embodiments, ΨPDK peptides and peptide compositions may be co-administered in a composition with a second therapeutic agent. In this manner, one skilled in the art will recognize that ΨPDK peptides individually, in combination, or combined with a second therapeutic agent, may be used to prepare a medicament for the slowing or inhibiting the progression of, for example, cardiovascular disease, or injury from cardiac ischemia, cardiac ischemia/reperfusion, myocardial infarction, chronic stable angina, acute coronary syndrome, or in complications resulting from a heart transplant.

VI. Formulations

A pharmaceutical composition comprising a described compound and at least one pharmaceutically acceptable excipient or carrier is provided. Methods of preparing such pharmaceutical compositions typically comprise the step of bringing into association a described compound with or without a carrier moiety and, optionally, one or more accessory ingredients. The described compounds and/or pharmaceutical compositions comprising same may be formulated into pharmaceutically-acceptable dosage forms by conventional methods known to those of skill in the art. Typically, formulations are prepared by uniformly and intimately bringing into association a described compound with liquid carriers, or finely divided solid carriers, or both, and then, if necessary, shaping the product. Pharmaceutical compositions of the present invention suitable for parenteral administration comprise one or more described compounds in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, amino acids, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These pharmaceutical compositions may also contain adjuvants such as preservatives, wetting agents, emulsifying agents and dispersing agents. Prevention of the action of microorganisms upon the described compounds may be ensured by the inclusion of various antibacterial and antifungal agents, for example, paraben, chlorobutanol, phenol sorbic acid, and the like. It may also be desirable to include agents to control tonicity, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

For example, a described compound may be delivered to a human in a form of solution that is made by reconstituting a solid form of the drug with liquid. This solution may be further diluted with infusion fluid such as water for injection, 0.9% sodium chloride injection, 5% dextrose injection and lactated ringer's injection. It is preferred that the reconstituted and diluted solutions be used within 4-6 hours for delivery of maximum potency. Alternatively, a described compound may be delivered to a human in a form of tablet or capsule.

Injectable depot forms are made by forming microencapsulated matrices of the described compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the described compounds are administered as pharmaceuticals, to humans and animals, they can be given alone or as a pharmaceutical composition containing, for example, 0.1 to 99% (more preferably, 10 to 30%) of active ingredient in combination with a pharmaceutically acceptable carrier. In other embodiments, the pharmaceutical composition may contain 0.2-25%, preferably 0.5-5% or 0.5-2%, of active ingredient. These compounds may be administered to humans and other animals for therapy by any suitable route of administration, including, e.g., subcutaneous injection, subcutaneous depot, intravenous injection, intravenous or subcutaneous infusion. These compounds may be administered rapidly (within <1 minute) as a bolus or more slowly over an extended period of time (over several minutes, hours or days). These compounds may be delivered daily or over multiple days, continuously or intermittently. In one embodiment, the compounds may be administered transdermally (e.g., using a patch, microneedles, micropores, ointment, microjet or nanojet).

Regardless of the route of administration selected, the described compounds, which may be used in a suitable hydrated form, and/or the pharmaceutical compositions, are formulated into pharmaceutically-acceptable dosage forms by conventional methods known to those of skill in the art.

Actual dosage levels of the active ingredients in the pharmaceutical compositions may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular described compound employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the described compounds employed in the pharmaceutical composition at levels lower than that required in order to achieve the desired therapeutic effect and gradually increase the dosage until the desired effect is achieved.

In general, a suitable daily dose of a described compound will be that amount of the compound which is the lowest dose effective to produce a therapeutic effect. Such an effective dose will generally depend upon the factors described above. Generally, intravenous, intramuscular, transdermal, intracerebroventricular and subcutaneous doses of the described compounds for a patient, when used for the indicated effects, will range from about 1 .mu.g to about 5 mg per kilogram of body weight per hour. In other embodiments, the dose will range from about 5 .mu.g to about 2.5 mg per kilogram of body weight per hour. In further embodiments, the dose will range from about 5 .mu.g to about 1 mg per kilogram of body weight per hour.

If desired, the effective daily dose of a described compound may be administered as two, three, four, five, six or more sub-doses administered separately at appropriate intervals throughout the day, optionally, in unit dosage forms. In one embodiment, the described compound is administered as one dose per day. In further embodiments, the compound is administered continuously, as through intravenous or other routes. In other embodiments, the compound is administered less frequently than daily, such as every 2-3 days, in conjunction with dialysis treatment, weekly or less frequently.

The subject receiving this treatment is any animal in need, including primates, in particular humans, and other mammals such as equines, cattle, swine and sheep; and poultry and pets in general.

The described compounds may be administered as such or in admixtures with pharmaceutically acceptable carriers and can also be administered in conjunction with antimicrobial agents such as penicillins, cephalosporins, aminoglycosides and glycopeptides. Conjunctive therapy thus includes sequential, simultaneous and separate administration of the active compound in a way that the therapeutical effects of the first administered one is not entirely disappeared when the subsequent is administered.

VII. Routes of Administration for Disclosed Compounds

These compounds may be administered to humans and other animals for therapy by any suitable route of administration. As used herein, the term "route" of administration is intended to include, but is not limited to subcutaneous injection, subcutaneous depot, intravenous injection, intravenous or subcutaneous infusion, intraocular injection, intradermal injection, intramuscular injection, intraperitoneal injection, intratracheal administration, intraadiposal administration, intraarticular administration, intrathecal administration, epidural administration, inhalation, intranasal administration, sublingual administration, buccal administration, rectal administration, vaginal administration, intracisternal administration and topical administration, transdermal administration, or administration via local delivery (for example by catheter or stent).

Transdermal drug delivery to the body is a desirable and convenient method for systemic delivery of biologically active substances to a subject, and in particular for delivery of substances that have poor oral bioavailability, such as proteins and peptides. The transdermal route of delivery has been particularly successful with small (e.g., less than about 1,000 Daltons) lipophilic compounds, such as scopolamine and nicotine, that can penetrate the stratum corneum outer layer of the skin, which serves as an effective barrier to entry of substances into the body. Below the stratum corneum is the viable epidermis, which contains no blood vessels, but has some nerves. Deeper still is the dermis, which contains blood vessels, lymphatics and nerves. Drugs that cross the stratum corneum barrier can generally diffuse to the capillaries in the dermis for absorption and systemic distribution.

Technological advances in transdermal delivery have focused on addressing the need in the art to deliver hydrophilic, high molecular weight compounds, such as proteins and peptides, across the skin. One approach involves disruption of the stratum corneum using chemical or physical methods to reduce the barrier posed by the stratum corneum. Skin microporation technology, which involves the creation of micron dimension transport pathways (micropores) in the skin (in particular, the micropores in the stratum corneum) using a minimally invasive technique, is a more recent approach. Techniques to create micropores in the skin (stratum corneum) include thermal microporation or ablation, microneedle arrays, phonophoresis, laser ablation and radiofrequency ablation (Prausnitz and Langer (2008) Nat. Biotechnology 11:1261-68; Arora et al., Int. J. Pharmaceutics, 364:227 (2008); Nanda et al. Current Drug Delivery, 3:233 (2006); Meidan et al. American J. Therapeutics, 11:312 (2004)).

In one embodiment, the modulator peptide is delivered via microporation. Any one of a number of techniques for microporation is contemplated, and several are briefly described.

Microporation can be achieved by mechanical means and/or external driving forces, to breach the stratum corneum to deliver the calcimimetic agents described herein through the surface of the skin and into the underlying skin layers and/or the bloodstream.

In a first embodiment, the microporation technique is ablation of the stratum corneum in a specific region of the skin using a pulsed laser light of wavelength, pulse length, pulse energy, pulse number, and pulse repetition rate sufficient to ablate the stratum corneum without significantly damaging the underlying epidermis. The calcimimetic agent is then applied to the region of ablation. Another laser ablation microporation technique, referred to as laser-induced stress waves (LISW), involves broadband, unipolar and compressible waves generated by high-power pulsed lasers. The LISWs interact with tissues to disrupt the lipids in the stratum corneum, creating intercellular channels transiently within the stratum corneum. These channel, or micropores, in the stratum corneum permit entry of the calcimimetic agent.

Sonophoresis or phonophoresis is another microporation technique that uses ultrasound energy. Ultrasound is a sound wave possessing frequencies above 20 KHz. Ultrasound can be applied either continuously or pulsed, and applied at various frequency and intensity ranges (Nanda et al., Current Drug Delivery, 3:233 (2006)).

Another microporation technique involves the use of a microneedle array. The array of microneedles when applied to a skin region on a subject pierce the stratum corneum and do not penetrate to a depth that significantly stimulates nerves or punctures capillaries. The patient, thus, feels no or minimal discomfort or pain upon application of the microneedle array for generation of micropores through which the modulatory agent is delivered.

Microneedle arrays comprised of hollow or solid microneedles are contemplated, where the modulatory agent can be coated on the external surface of the needles or dispensed from the interior of hollow needles. Examples of microneedle arrays are described, for example, in Nanda et al., Current Drug Delivery, 3:233 (2006) and Meidan et al. American J. Therapeutics, 11:312 (2004). First generation microneedle arrays were comprised of solid, silicon microneedles that were externally coated with a therapeutic agent. When the microarray of needles was pressed against the skin and removed after about 10 seconds, the permeation of the agent on the needles into the body was readily achieved. Second generation microneedle arrays were comprised of microneedles of solid or hollow silicon, polycarbonate, titanium or other suitable polymer and coated or filled with a solution of the therapeutic compound. Newer generations of microneedle arrays are prepared from biodegradable polymers, where the tips of the needles coated with a therapeutic agent remain in the stratum corneum and slowly dissolve.

The microneedles can be constructed from a variety of materials, including metals, ceramics, semiconductors, organics, polymers, and composites. Exemplary materials of construction include pharmaceutical grade stainless steel, gold, titanium, nickel, iron, tin, chromium, copper, palladium, platinum, alloys of these or other metals, silicon, silicon dioxide, and polymers. Representative biodegradable polymers include polymers of hydroxy acids such as lactic acid and glycolic acid polylactide, polyglycolide, polylactide-co-glycolide, and copolymers with poly(ethylene glycol), polyanhydrides, poly(ortho)esters, polyurethanes, poly(butyric acid), poly(valeric acid), and poly(lactide-co-caprolactone). Representative non-biodegradable polymers include polycarbonate, polyester, and polyacrylamides.

The microneedles can have straight or tapered shafts. In one embodiment, the diameter of the microneedle is greatest at the base end of the microneedle and tapers to a point at the end distal the base. The microneedle can also be fabricated to have a shaft that includes both a straight (untapered) portion and a tapered portion. The needles may also not have a tapered end at all, i.e. they may simply be cylinders with blunt or flat tips. A hollow microneedle that has a substantially uniform diameter, but which does not taper to a point, is referred to herein as a "microtube." As used herein, the term "microneedle" includes both microtubes and tapered needles unless otherwise indicated.

Electroporation is another technique for creating micropores in the skin. This approach uses the application of microsecond or millisecond long high-voltage electrical pulses to created transient, permeable pores within the stratum corneum.

Other microporation techniques include use of radio waves to create microchannels in the skin. Thermal ablation is yet another approach to achieve delivery of larger molecular weight compounds transdermally.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not necessarily to the text of this application, in particular the claims of this application, in which instance, the definitions provided herein are meant to supercede.

The following examples are put forth so as to provide those of ordinary skill in the art with a complete disclosure and description of how to implement the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

EXAMPLES

Example 1

Materials

Cell Culture.

Fibroblasts were isolated from wild-type or δPKC knockout mice (provided by Dr. Robert Messing, Gallo Center, UCSF) as previously described (Disatnik et al., 2004, J. Cell Sci., 117:4469-4479) and maintained in 20% fetal bovine serum.

Peptide Synthesis.

Peptides were synthesized using Microwave by Liberty Microwave Peptide Synthesizer (CEM Corporation, Matthews, N.C., USA) or by American Peptide (CA, USA). Peptides were conjugated to TAT carrier by disulfide bond as described in Chen et al. (2001, Chem. Biol., 8:1123-1129) or synthesized as one polypeptide:

N-terminus-TAT-spacer-cargo-C-terminus

The C-terminus of the peptides was modified to C(O)—$NH_2$ using Rink Amide AM resin to increase stability (as described in Sabatino et al. (Cur. Opin. in Drug Disc. & Dev., 11:762-770). Peptides were analyzed by analytical reverse-phase high-pressure liquid chromatography (RP-HPLC) (Shimadzu, Md., USA) and matrix-assisted laser desorption/ionization (MALDI) mass spectrometry (MS) and purified by preparative RP-HPLC (Shimadzu, Md., USA).

PKC Substrate Phosphorylation in Fibroblasts.

Phosphorylation of myristoylated alanine-rich C kinase substrate (MARCKS), a ubiquitous PKC substrate, was monitored by Western blot of total cell lysates, using anti-phosphorylated MARCKS (Cell Signaling, Danvers, Mass.). Anti-MARCKS and anti-δPKC antibodies were obtained from Santa Cruz Biotechnology (Santa Cruz Biotechnology, CA, USA).

Ex Vivo Cardiac Protection for Ischemia/Reperfusion (I/R).

An ex vivo model of acute ischemic heart damage was used, which involves a 30 min equilibration period, followed by 30 min of global ischemia, which in turn is followed by 60 min of reperfusion. The hearts were perfused with 1 μM TAT or TAT-conjugated peptide. Normoxic control hearts were subjected to 90 min perfusion in the absence of ischemia. Coronary effluent was collected to determine creatine phosphokinase (CPK) release during the first 30 min of the reperfusion period. At the end of the reperfusion period, hearts were sliced into 1-mm-thick transverse sections and incubated in triphenyltetrazolium chloride solution (TTC, 1% in phosphate buffer, pH 7.4) at 37° C. for 15 min. Infarct size was expressed as a percentage of the risk zone (equivalent to total LV muscle mass) (methods described in Brandman et al., 2007, J. Biol. Chem., 282:4113-4123; Inagaki et al., 2003, Circulation, 108:869-875).

Western Blot Analysis and 2D Analysis.

Rat hearts were homogenized in a buffer containing 210 mM mannitol, 70 mM sucrose, 5 mM MOPS and 1 mM EDTA followed by isolation of the mitochondria fraction (described in Churchill et al., 2008, J. Mol. Cell. Cardiol., 46:278-284) and identified by the presence of VDAC (Mito- Sciences, Eugene, Oreg., USA). The level of phosphorylated and unphosphorylated JNK1/2 was analyzed in the total fraction using respective specific antibodies (Cell Signaling, Danvers, Mass. and Santa Cruz Biotechnology, CA, USA).

2-D IEF/SDS polyacrylamide gel electrophoresis using rat heart samples was performed as previously described (Chen et al., 2008, Science, 321:1493-1495). 10% SDS gel electrophoresis and Western blotting were carried out by standard methods using PDK2 c-term rabbit (Abgent, Calif., USA), PDH subunit E1 alpha monoclonal (Invitrogen, Calif., USA) and ALDH2 goat (Santa Cruz Biotechnology, CA, USA) antibodies.

In vitro phosphorylation assay. To determine the level of PDK and Drp1 phosphorylation in presence of ΨPDK, δPKC recombinant protein (Invitrogen, Calif., USA; 200 ng) was incubated with or without peptides for 10 min, then 100 ng recombinant PDK2 (Abnova, Taiwan) or Drp1 (Abnova, Taiwan) were added for 20 min at 37° C. in 40 µl of kinase buffer (20 mM Tris-HCl, 20 mM $MgCl_2$, 1 µM DTT, 25 µM ATP, 1 mM $CaCl_2$) containing 5 µCi [$\gamma^{32}P$] ATP (4500 Ci/mmol, ICN) in the presence of the low amount of PKC activators, phosphatidylserine (PS, 1.25 µg) and 1,2 dioleoyl sn-glycerol (DG, 0.04 µg). The kinase assay was terminated by adding loading Laemmli buffer containing 5% SDS and the samples were loaded on a 10% PAGE-SDS polyacrylamide gel, and the levels of phosphorylated PDK2 protein were determined by exposing the nitrocellulose to autoradiography. The nitrocellulose was also reprobed using respective antibodies for loading controls.

Proteinase K Digestion.

To determine whether δPKC protein is located in the inner or outer membrane of mitochondria after I/R injury, we isolated mitochondria as described above from heart subjected to 30 min ischemia followed by 60 min reperfusion. The respective mitochondrial extract (200 µg) was treated with 50 µg/ml of proteinase K (stock concentration 20 mg/ml, Invitrogen, Calif., USA). The digestion was stopped by the addition of 5 mM phenylmethylsulfonyl fluoride (PMSF). Equal amounts of proteins were loaded on a 10% SDS gel and probed for δPKC as well as MFN1 (outer mitochondrial marker) and ALDH2 (mitochondrial matrix marker). To determine that δPKC is sensitive to proteinase K digestion, the mitochondrial fraction was solubilized with 1% Triton X-100 and used as a control in the same assay.

Human recombinant δPKC (Invitrogen, Calif., USA; 50 ng; 0.625 pmole) was incubated with ΨPDK (non-TAT conjugated, 1 nmole) prior to addition of proteinase K (0.05 µg/ml) in 20 mM Tris-HCl, pH 7.4 containing 1 µM DTT. The reaction was stopped as indicated by adding 5 mM PMSF.

Statistical Methods.

Data are expressed as mean±S.E. Unpaired t test was used to define statistical differences ($p<0.05$) between 2 groups.

Example 2

Rational Design of a Peptide Based on Homology Between δPKC and PDK

Figures 1B, 1C:
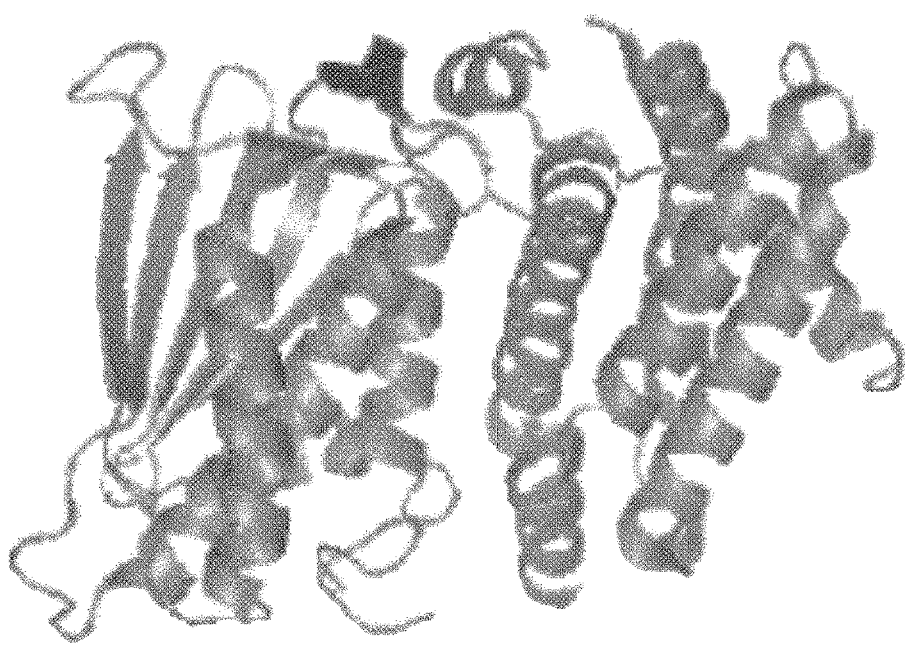
FIG. 1B illustrates an amino acid sequence alignment of a partial sequence from human PDK2 with a partial sequence of human δPKC from various species.
FIG. 1C illustrates a 3D structure of PDK2.
Figure 1G:
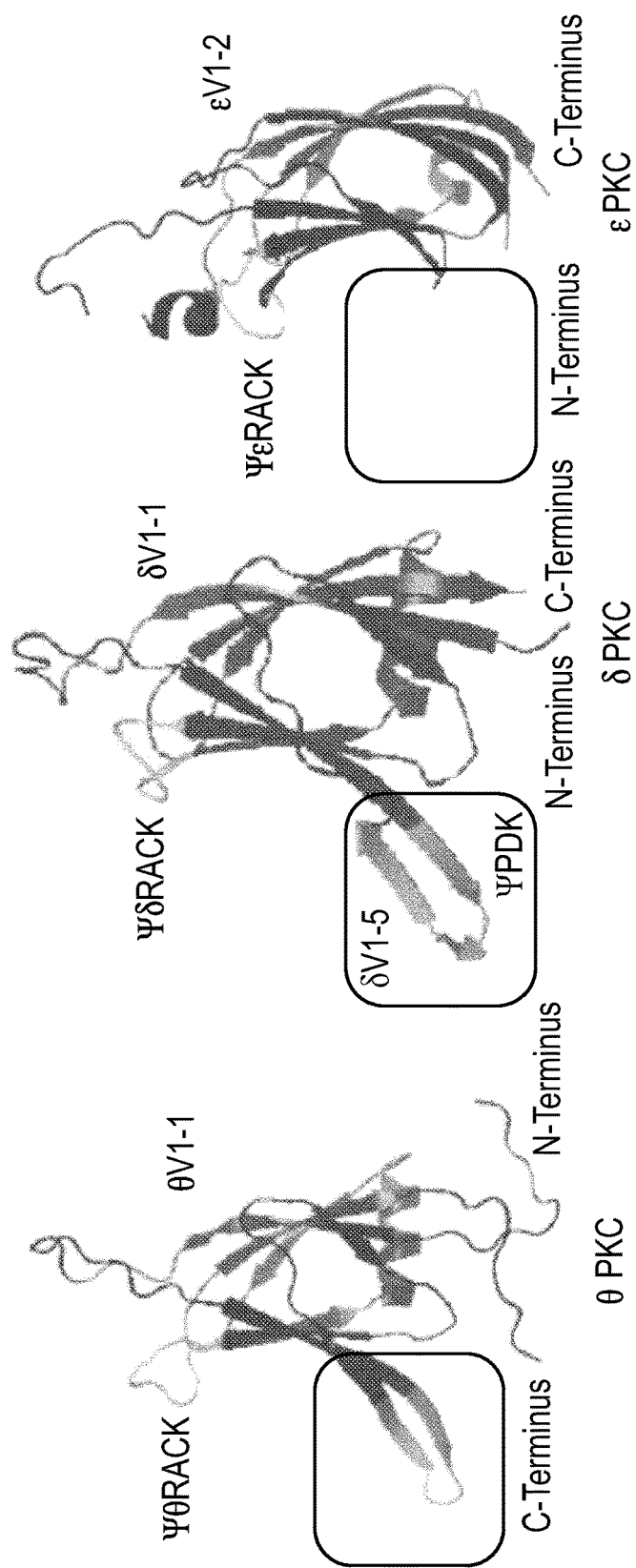
FIG. 1G illustrates secondary structures for the θ-, δ-, and ε-PKC proteins.

It was reasoned that similar to the pseudo-substrate sites (House et al., 1987, Science, 238:1726-1728) and pseudo-RACK sites (Dorn et al., 1999, Proc. Natl. Acad. Sci., 96:12798-12803; Ron et al., 1995, Proc. Natl. Acad. Sci., 92:492-496) on each PKC that are homologous to the corresponding PKC-interacting proteins, there might be a PDK-like sequence in δPKC. A sequence homology search using Lalign (Huang et al., 1991, Adv. appl. Math., 12:337-357) identified a five amino acid stretch in PDK (ALSTD (SEQ ID NO:5); amino acids 391-395) that is almost identical to a sequence in δPKC (ALSTE (SEQ ID NO:1), amino acids 35-39; FIG. 1B). Interestingly, the ALSTD (SEQ ID NO:5) sequence in the PDK structure is located in an exposed region available for protein-protein interaction (FIG. 1B). One of the criteria established for the identification of sequences that are critical for protein-protein interactions is their conservation in evolution (Souroujon et al., 1998, Nat. Biotechnol., 16:919-924; Qvit et al., 2010, Drug Disc. Today: Dis. Mech., 7:e87-e93). The ALESTE/D (SEQ ID NO:56) sequence in δPKC and in PDK is conserved in all the species that have PKC isozymes (FIG. 1C, D). Supported by the above rationale, in species that lack δPKC, the sequence contains an extra negative charge (e.g., Drosophila, FIG. 1D) or is missing altogether (e.g., worm and yeast; FIG. 1D, bottom).

Unexpectedly, ALSTE (SEQ ID NO:1) is found within the C2 domain of δPKC, the domain already found to be critical in protein-protein interactions for PKC (Smith et al., 1992, Biochem. biophys. Res. Commun., 188:1235-1240; Johnson et al., 1996, J. Biol. Chem., 271:24962-24966; Brandman et al., 2007, J. Biol. Chem., 282:4113-4123) and to contain the isozyme-specific inhibitors (e.g., εV1-2, δV1-1 and θV1-2; FIG. 1E) and activators (ΨεRACK, ΨδRACK and ΨθRACK; FIG. 1E). Importantly, ALSTE (SEQ ID NO:1) is not found in εPKC or θPKC (θPKC is the isozyme most homologous to δPKC (Baier et al., 1993, J. Biol. Chem., 268:4997-5004), FIG. 1E); ALSTE (SEQ ID NO:1) in δPKC is a part of a unique β hairpin found also in θPKC and is missing in other PKC isozymes, including εPKC (FIG. 1F, boxed area).

Figure 2A:
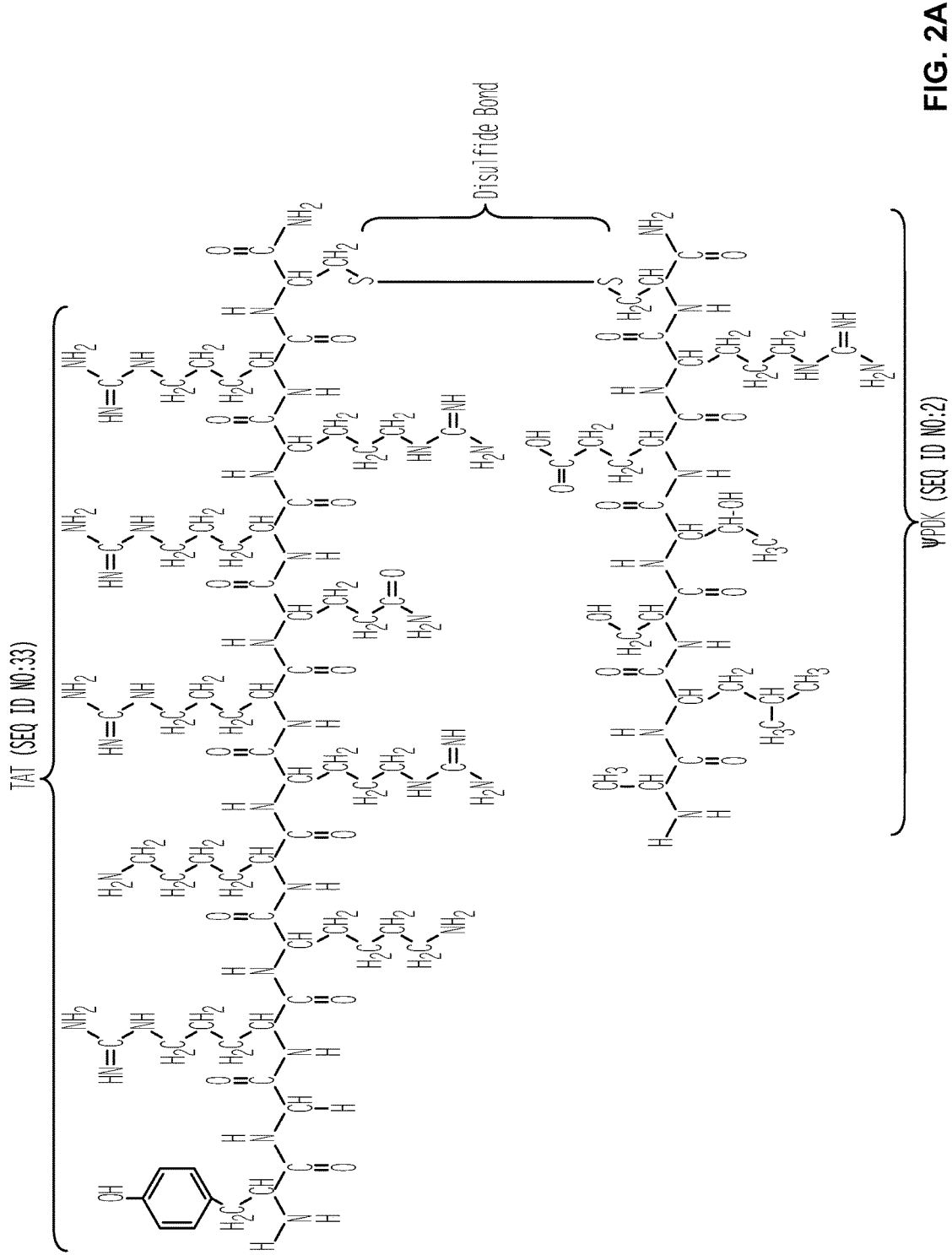
FIG. 2A illustrates the chemical structure of a ΨPDK peptide (SEQ ID NO:2; ALSTER) linked to a TAT peptide (SEQ ID NO:33; YGRKKRRQRRR) via a disulfide bond. A cysteine residue is present (via a peptide bond) at the C-terminus of SEQ ID NO:33 and at the C-terminus of SEQ ID NO:2.
Figure 2B:
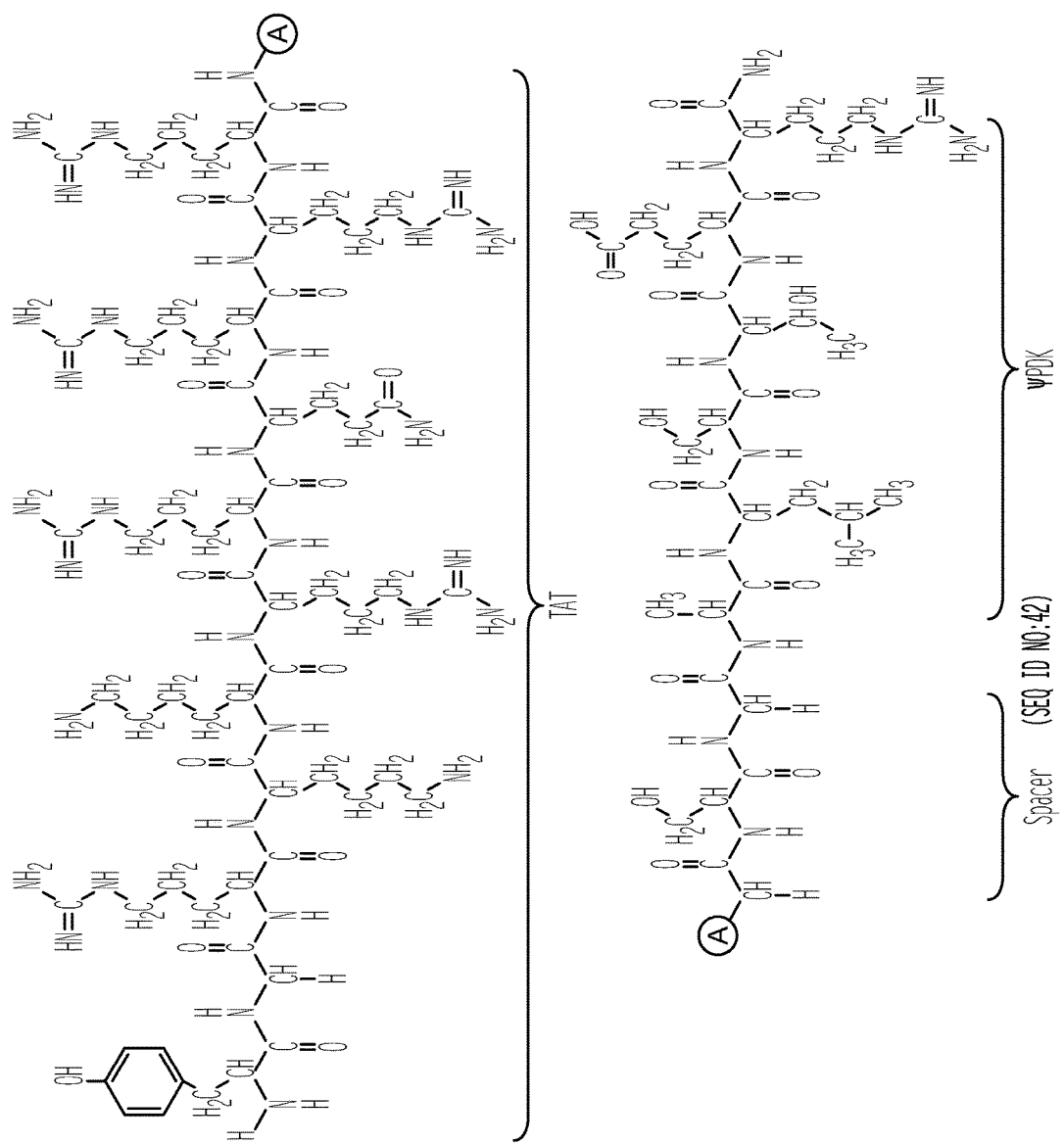
FIG. 2B illustrates the chemical structure of a ΨPDK peptide linked to a TAT peptide via a peptide bond and GSG spacer (SEQ ID NO:42; YGRKKRRQRRRGSGALSTER.

To determine whether this sequence is involved in δPKC regulation of PDK, the corresponding peptide was synthesized. Because it has been previously observed that a minimal length of biologically active peptide inhibitors of protein-protein interactions may be six amino acids, we extended ALSTE (SEQ ID NO:1) by one amino acid, R (ALSTER, SEQ ID NO:2). This peptide is referred to herein as ΨPDK. The δV1-5 peptide, which completes the β hairpin in δPKC (FIG. 1E-F boxed area), was synthesized as a control peptide (GKTLVQ; SEQ ID NO:4). To facilitate delivery of the peptides into cells, the peptides were conjugated to the TAT-derived cell permeating peptide, $TAT_{47-57}$ (SEQ ID NO:33) via a disulfide bond between cysteine residues positioned at the C-terminus of each of the modulatory or control peptide and the carrier peptides (FIG. 2A).

Example 3

ΨPDK is Specific for δPKC; A Study in Cultured Fibroblasts

Figure 2C:
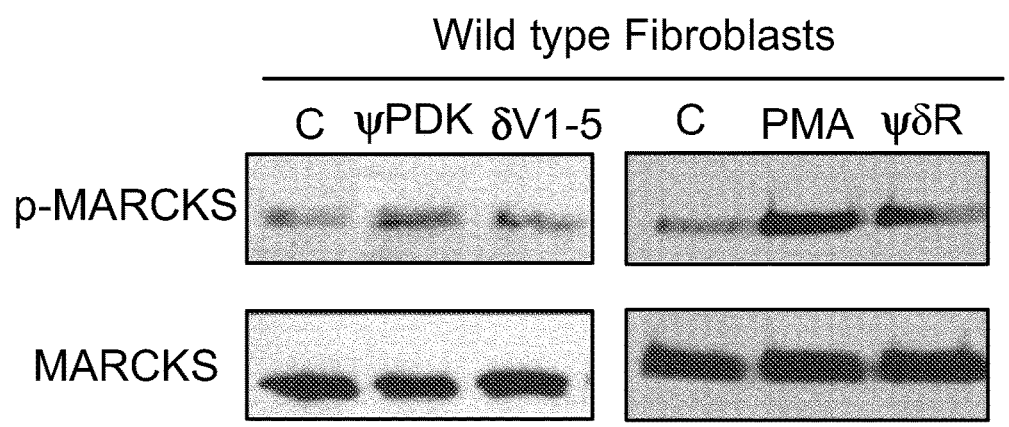
FIGS. 2C-D are western blots showing effects of various peptides on MARCKS phosphorylation in wildtype fibroblasts (FIG. 2C) or in fibroblasts from δPKC knock-out mice (FIG. 2D).
Figure 2D:
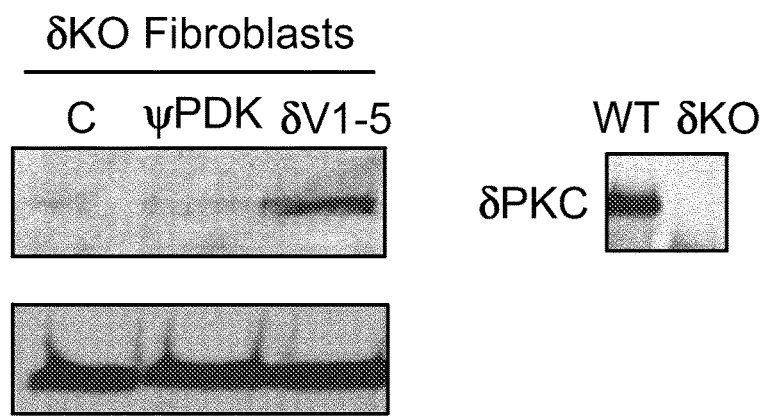

The ΨPDK sequence is found both in PDK and in the PDK-cognate protein, δPKC. It was therefore predicted that ΨPDK mimics inhibitory intra-molecular interaction, and, similar to ΨδRACK, ΨPDK should compete with the inhibitory interaction of PDK and δPKC, and increase δPKC-mediated functions (FIG. 1A). Phosphorylation of myristoylated alanine-rich C-kinase substrate (MARCKS) was used as a marker of PKC activity (Disatnik et al., 2004, J. Cell. Sci., 117:4469-4479). Incubation of cells cultured in media containing 20% serum (which primes PKC for activation (Disatnik et al., 2004, J. Cell. Sci., 117:4469-4479)) with either ΨPDK (FIG. 2A) or with δV1-5 (each conjugated to $TAT_{47-57}$ to facilitate their delivery into cells) increased MARCKS phosphorylation relative to the control peptide (FIG. 2C, left). Phorbol 12-myristate 13-acetate (PMA), a potent activator of PKC or ΨδRACK, used as positive controls, also caused increased MARCKS phosphorylation (FIG. 2C, right). To determine the selectivity of the peptides for δPKC, fibroblasts derived from δPKC knockout mice were also used. Whereas δV1-5 increased MARCKS phosphorylation in these cells, ΨPDK did not affect MARCKS phosphorylation in cells lacking δPKC (FIG. 2D, 2D insert). These data demonstrate that the δPKC-derived peptides, ΨPDK and δV1-5, are activators of δPKC phosphorylation of MARCKS, but only ΨPDK is specific for δPKC; δV1-5 probably affects multiple PKC isozymes.

Example 4

ΨPDK Specifically Inhibits PDK Phosphorylation by δPKC, In Vitro

Figures 3A, 3B:
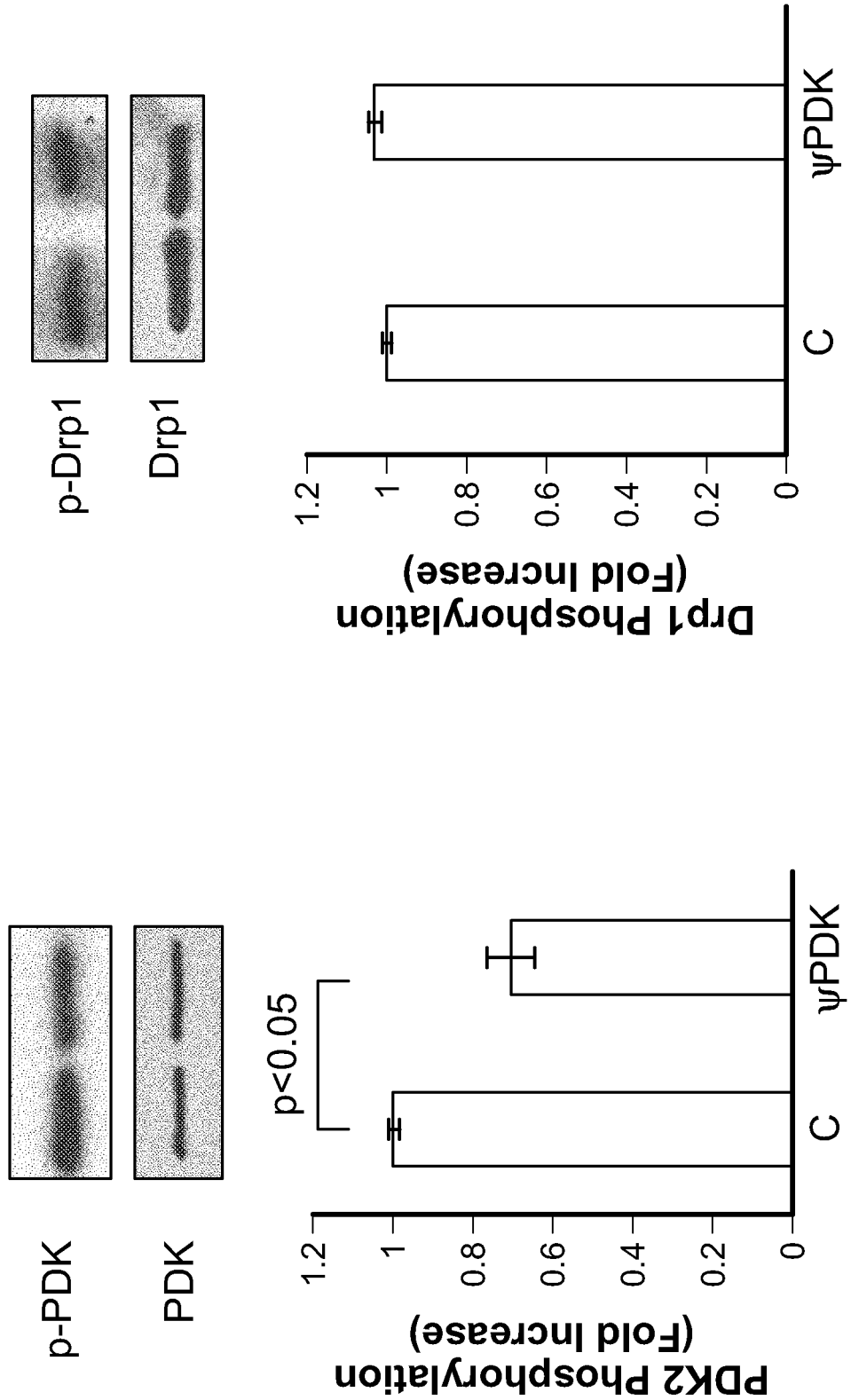
FIGS. 3A-B demonstrate the effects of a ΨPDK peptide on phosphorylation of PDK2 (FIG. 3A) or Drp1 (FIG. 3B) by δPKC.
Figures 3C, 3D:
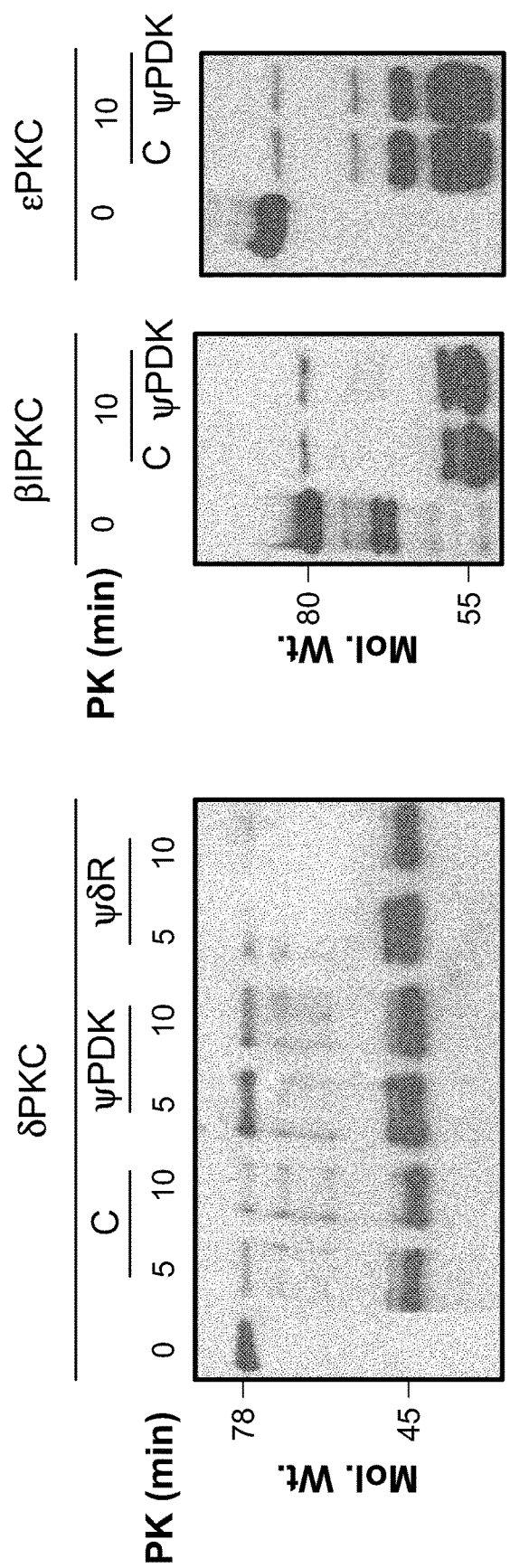
FIGS. 3C-D demonstrate the effects of a ΨPDK peptide on sensitivity of δPKC (FIG. 3C), βI-PKC (FIG. 3D) or εPKC (FIG. 3D) to proteolysis by proteinase K (PK).

Since ΨPDK is derived from a PDK-like sequence in δPKC (FIG. 1B), it was reasoned that this peptide should act as a competitive inhibitor, selective for δPKC phosphorylation of PDK. To test this hypothesis directly, an in vitro kinase assay in which the ability of δPKC to phosphorylate PDK is determined was used. Whereas ΨPDK inhibited δPKC phosphorylation of PDK by ~30%, the control peptide did not (FIG. 3A). The selectivity of ΨPDK for PDK was determined by examining the in vitro phosphorylation of Drp1, another δPKC substrate (Qi et al, 2010, Mol. Biol. Cell., 22:256-265) and it was found that ΨPDK did not affect Drp1 phosphorylation (FIG. 3B). Together these data suggest that ΨPDK is a specific inhibitor of PDK phosphorylation by δPKC. FIG. 3C demonstrates that ΨPDK directly binds δPKC since the peptide altered the sensitivity of δPKC to proteolysis. Proteinase K (PK) assays showed that human recombinant protein δPKC is more stable to PK digestion in the presence of ΨPDK as compared with no peptide or control peptide, ΨδRACK. ΨPDK-induced resistance to PK degradation of δPKC was specific; the sensitivity of εPKC or β$_I$PKC to proteolysis by PK were unaffected by the presence of ΨPDK.

Example 5

ΨPDK Increases the Translocation of δPKC into the Mitochondria in Intact Hearts Subjected to Ischemia and Reperfusion (I/R)

Figure 4A:
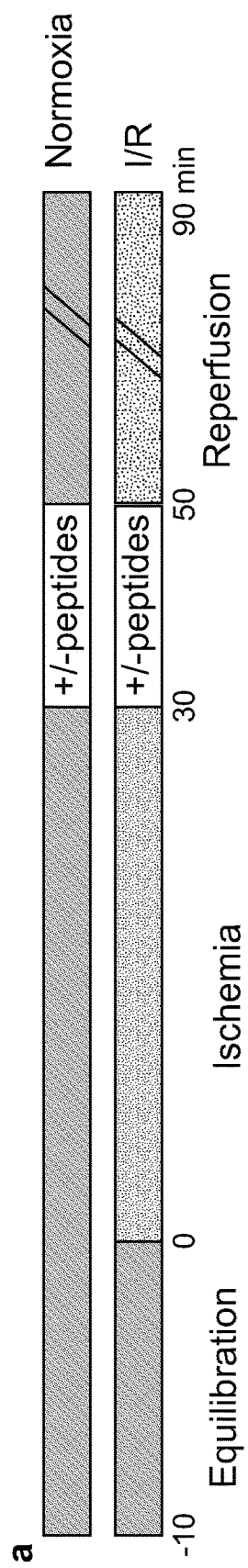
FIG. 4A is a schematic showing a time frame for a protocol involving ischemia and reperfusion to mimic myocardial infarction in the presence (+) or absence (−) of a peptide.
Figure 4B:
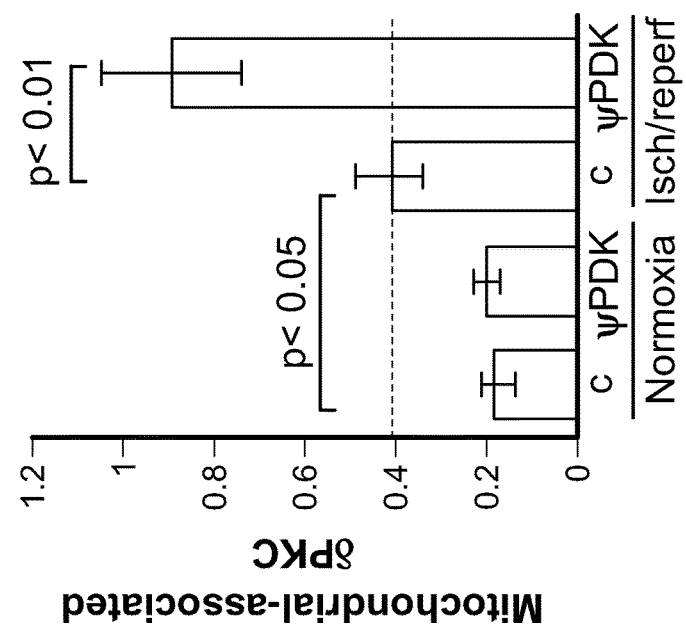
FIG. 4B illustrates effects of a ΨPDK peptide on I/R-induced translocation of δPKC.
Figure 4C:
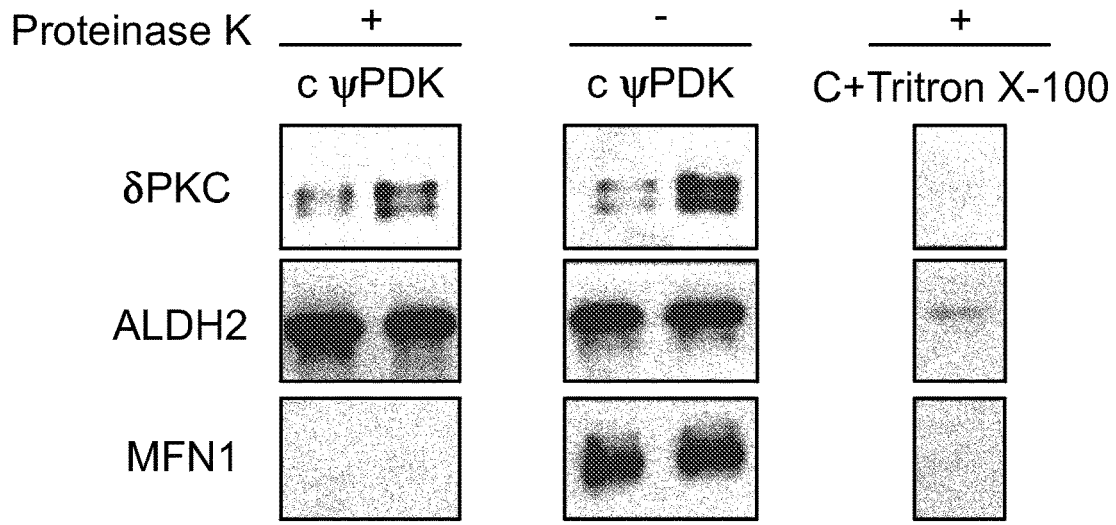
FIGS. 4C-D illustrate results of assays using proteinase K to demonstrate entry of δPKC into the mitochondria following treatment with a ΨPDK peptide.
Figure 4D:
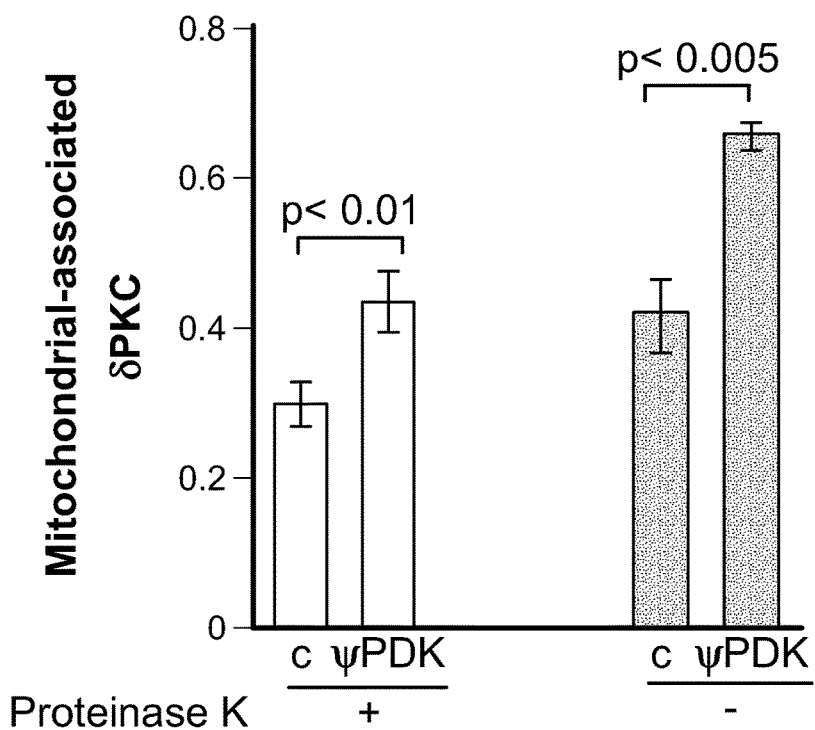

Phosphorylation of the mitochondrial PDK by δPKC occurs only following myocardial infarction Under these conditions, δPKC translocates into the mitochondria (Churchill et al., 2005, Circ. Res., 97:78-85) where it has access to PDK. It was therefore first determined whether ΨPDK peptide affects δPKC translocation into the mitochondria. Following ischemia and reperfusion (I/R) conditions, which mimic myocardial infarction (FIG. 4A), there was a two-fold increase in δPKC association with the mitochondria when the hearts were treated with ΨPDK, as compared with heart treated with control peptide (FIG. 4B). We also found that ΨPDK did not induce δPKC translocation to the mitochondria under normoxic condition. To determine if δPKC entered the mitochondria following ΨPDK treatment, the above intact cardiac mitochondria were subjected to proteinase K treatment. The outer membrane protein, mitofusion 1 (MFN1), was completed degraded (FIG. 4C, lower panel). However, similar to the mitochondrial matrix protein, aldehyde dehydrogenase (ALDH2), the majority of δPKC was insensitive to proteolysis by PK (FIG. 4C; quantitated in FIG. 4D). These data indicate that ΨPDK increased I/R-induced δPKC entry into the mitochondria.

Example 6

Figure 5A:
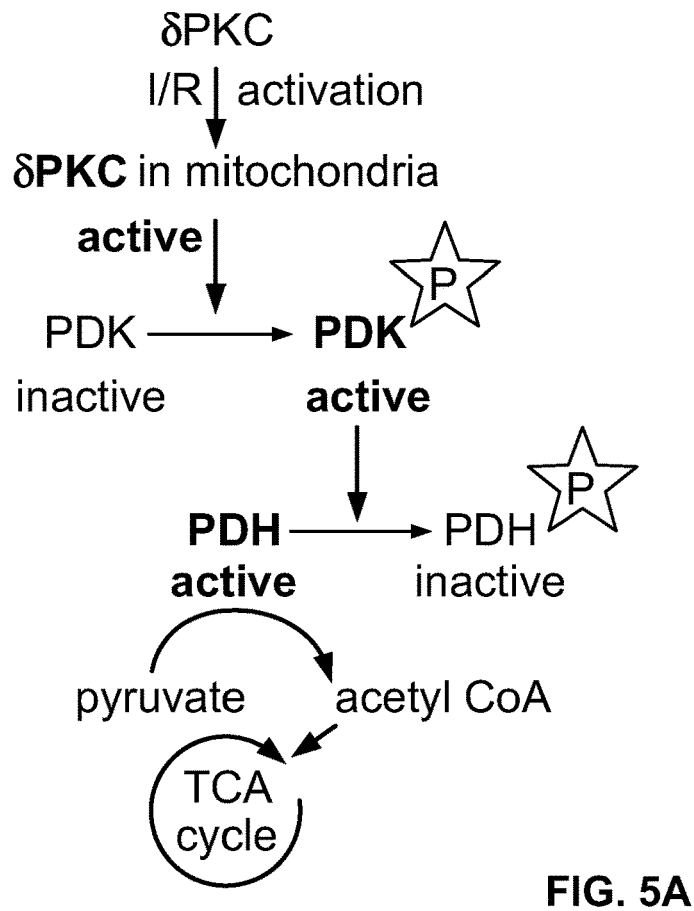
FIG. 5A is a schematic summarizing the cascade of events following δPKC activation by I/R.
Figure 5B:
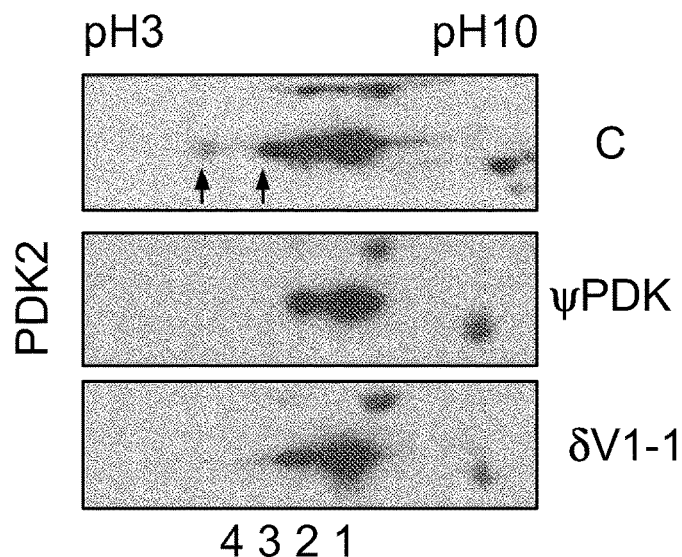
FIGS. 5B-D shows results of 2-D IEF gel assays to measure phosphorylation of PDK2 (FIG. 5B), PDH (FIG. 5C) and ALDH2 (FIG. 5D).
Figure 5C:
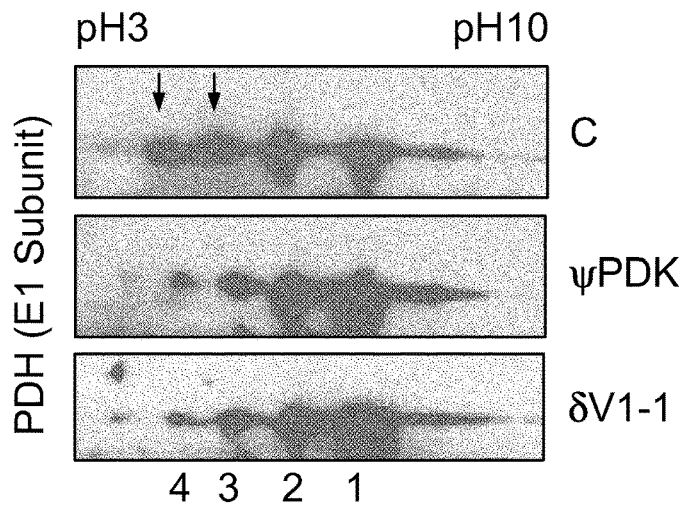
Figure 5D:
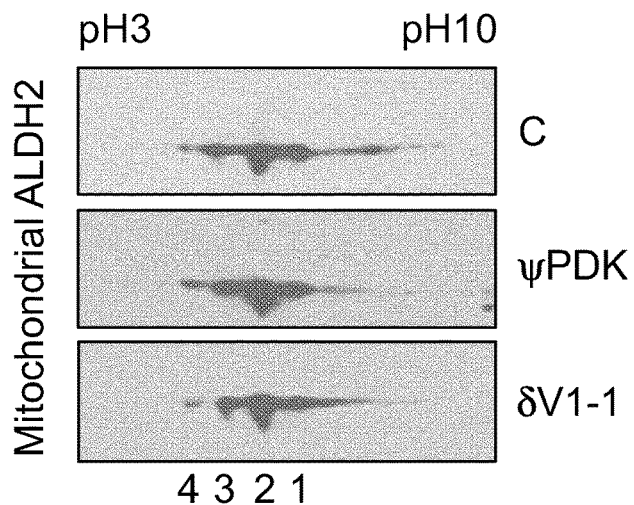

ΨPDK Selectively Inhibits the Phosphorylation of the δPKC Substrate, Pyruvate Dehydrogenase Kinase Following I/R As described above, δPKC phosphorylation of PDK following cardiac ischemia and reperfusion leads to the phosphorylation and a decline in the activity of pyruvate dehydrogenase (PDH) (Churchill et al., 2005, Circ. Res., 97:78-85). Thus, PDK phosphorylation of PDH leads to reduction in acetyl CoA production, which is required for the TCA cycle and ATP generation (FIG. 5A). Since ΨPDK is derived from the PDK homologous sequence in δPKC, it was next determined whether PDK phosphorylation is affected by ΨPDK treatment. As reported before (Churchill et al., 2005, Circ. Res., 97:78-85), using two dimensional isoelectric-focusing (2-D IEF), it was found that cardiac I/R resulted in increased phosphorylation of PDK2 (FIG. 5B; arrows) and the subsequent phosphorylation of the E1 subunit of PDH (FIG. 5C; arrows). However, the phosphorylation of those two enzymes (shown by a shift to acidic pH by 2-D IEF analysis) did not occur in the presence of either ΨPDK or in the presence of δV1-1, the δPKC-specific inhibitor (FIG. 5B-C) (Chen et al., 2001, Proc. Natl. Acad. Sci., 98:11114-11119).

To determine whether ΨPDK inhibition was selective for δPKC-mediated phosphorylation when inside the mitochondria, the phosphorylation state of aldehyde dehydrogenase 2 (ALDH2), an εPKC-selective mitochondrial substrate (Chen et al., 2008, Science, 321:1493-1495), was also examined. As expected for isozyme-specific peptide regulators, neither ΨPDK nor δV1-1 affected ALDH2 phosphorylation (FIG. 5D), demonstrating a selective effect of the peptide for δPKC.

Figure 5E:
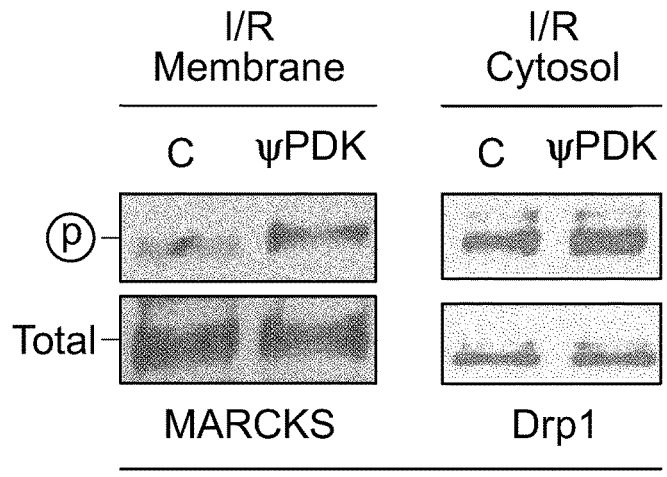
FIG. 5E shows results of a phosphorylation assay to measure phosphorylation of MARCKS (left panel) and Drp1 (right panel) in hearts subjected to I/R with or without a ΨPDK peptide.

Finally, under the same cardiac I/R conditions, ΨPDK did not inhibit the phosphorylation of the membrane bound substrate, MARCKS; rather an increase in I/R-induced MARCKS phosphorylation was observed in the presence of ΨPDK, as compared with control peptide. Moreover, ΨPDK also caused an increase of Drp1 phosphorylation in these hearts subjected to I/R (FIG. 5E). Together, these data indicate that, similar to the in vitro kinase assay (FIG. 3A), ΨPDK acted as an inhibitor of PDK phosphorylation at the mitochondria. Importantly ΨPDK did not affect the phosphorylation of other δPKC substrates in other subcellular compartments under the same conditions (FIG. 3B, 5E).

Example 7

ΨPDK Peptide Treatment Induces Heart Protection in an Ex Vivo Model of Heart Attack Because ΨPDK inhibited δPKC-mediated phosphorylation of PDK, but not the phosphorylation of other δPKC substrates, the role of δPKC-mediated ΨPDK phosphorylation in cardiac ischemia and reperfusion injury was next determined. Using the Langendorff preparation (Langendorff, 1895, Pflügers Archiv, 61:291-382; Hondeghem et al., 1978, Amer. J. Physiol., 235:H574-H580), it was previously found that activation of δPKC leads to increased ischemic injury to the myocardium (Chen et al., 2001, Proc. Natl., Acad., Sci. 98:11114-11119). If PDK phosphorylation is critical for δPKC-mediated function, it would be expected that ΨPDK, which selectively inhibits PDK phosphorylation without affecting the phosphorylation of other δPKC substrates, would protect the myocardium from I/R-induced injury.

Using three criteria, it was confirmed that ΨPDK treatment induced cardiac protection following I/R, as compared to control peptides (FIG. 6). First, I/R-induced infarct size after treatment with ΨPDK or δV1-1 (Inagaki et al., 2003, Circulation, 108:869-875), was smaller than that in hearts treated with the control peptide or with ΨδRACK, the δPKC-specific activator or with δV1-5 (FIG. 6A). Second, similar data were obtained when determining the levels of released creatine phosphokinase (CPK), as a marker of myocardial infarction; CPK levels in the ΨPDK- or δV1-

Figures 6A, 6B:
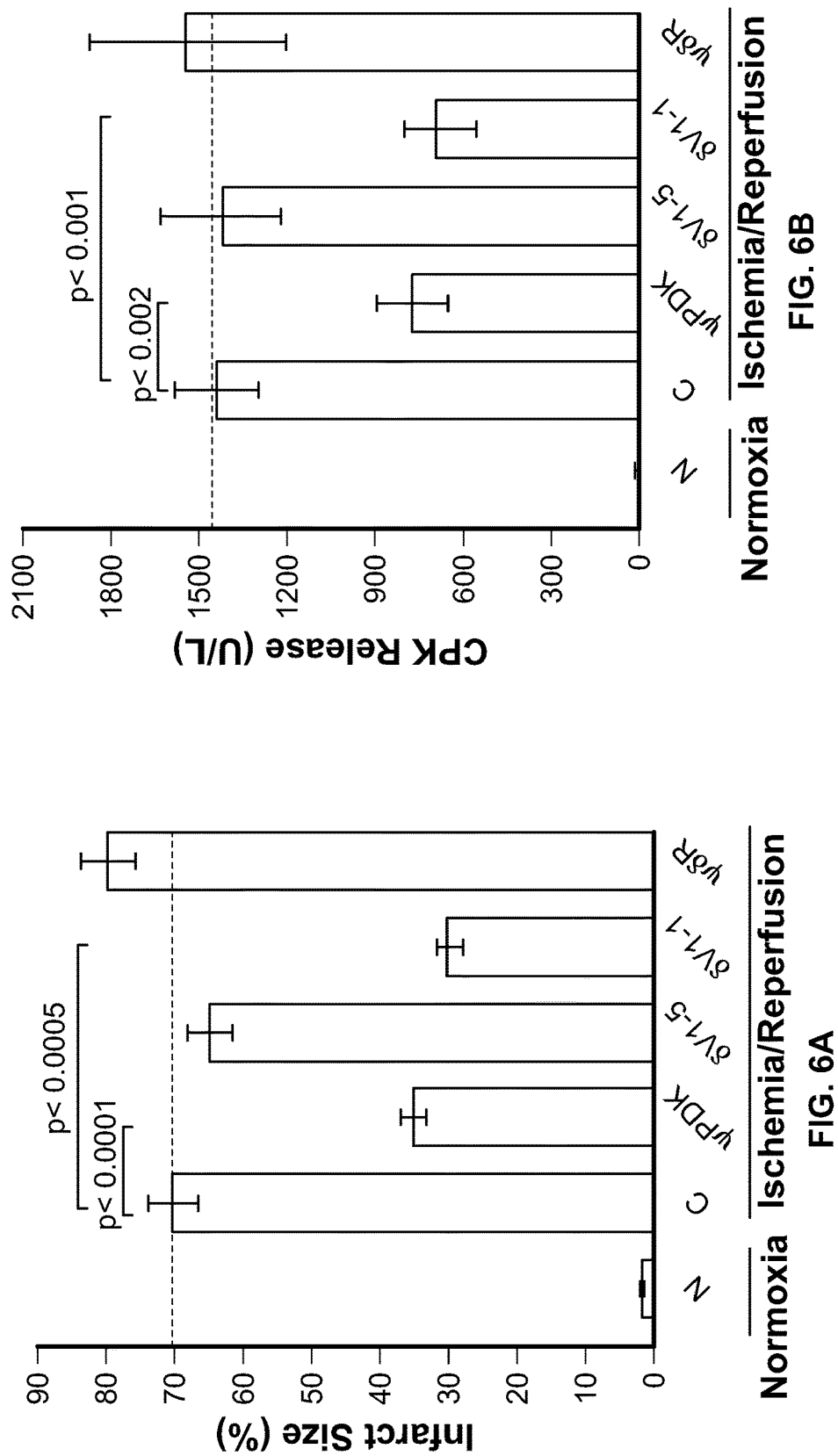
FIG. 6A shows effect of treatment with a ΨPDK peptide on infarct size in heart tissue.
FIG. 6B is a graph showing levels of CPK released by hearts subject to I/R injury into the perfusate during the first 30 min. of reperfusion.
Figure 6D:
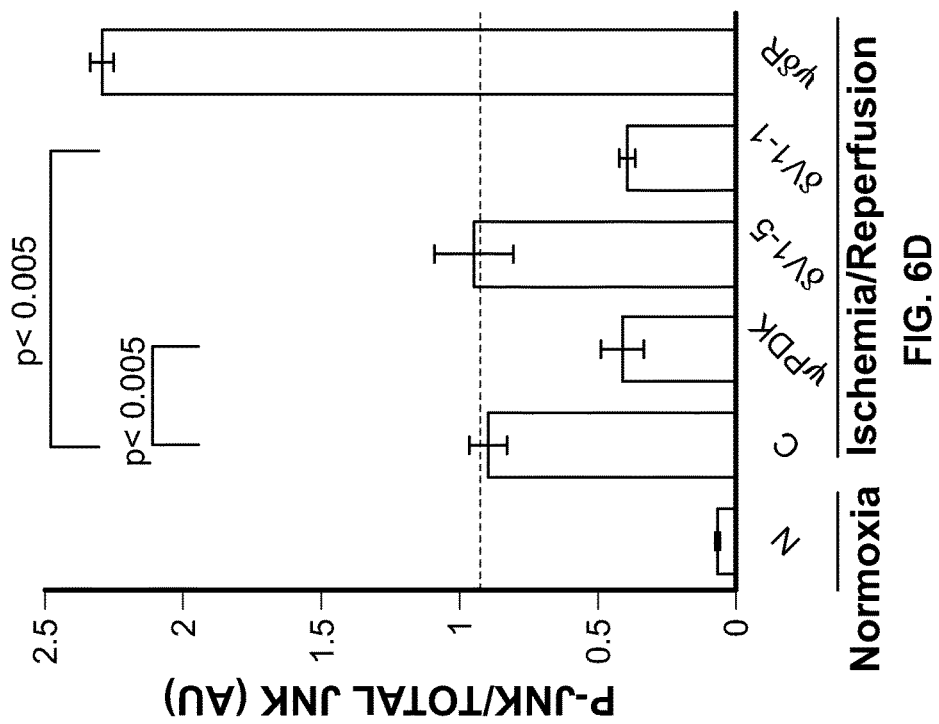
FIG. 6C-D shows results of western blot analysis of phosphorylated JNK and total JNK in hearts subjected to I/R injury followed by reperfusion. Quantitation of the results is shown in FIG. 6D.
Figure 6C:
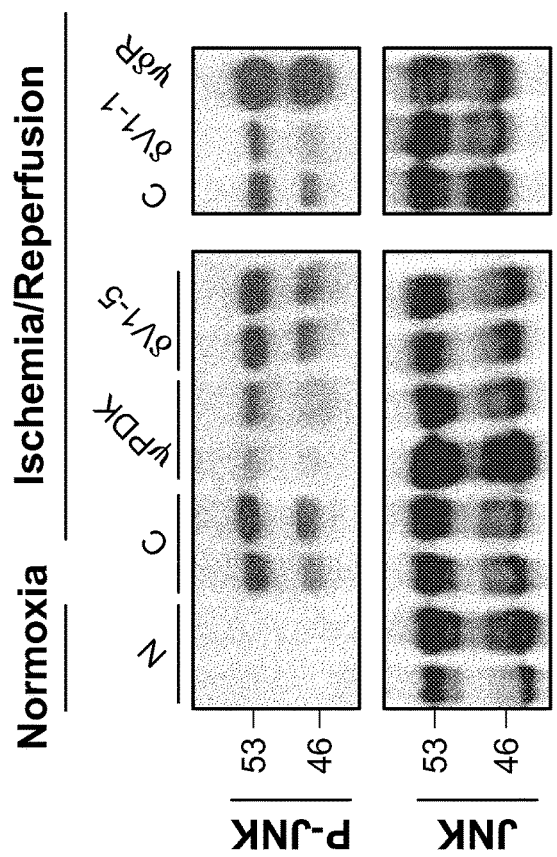

1-treated hearts were similar and were lower than those after treatment with control peptide, ΨδRACK or δV1-5 (FIG. 6B). Finally, the levels of JNK protein phosphorylation, a known marker of cellular stresses and apoptosis (Davis et al., 2000, Cell, 103:239-252), were determined. δV1-1 and ΨPDK reduced I/R-induced JNK phosphorylation as compared with the other δPKC-derived peptides, δV1-5 and ΨδRACK (FIGS. 6C and 6D). Together, these data indicate that ΨPDK, the selective inhibitor of PDK phosphorylation, was sufficient to inhibit I/R injury.

Figures 6E, 7:
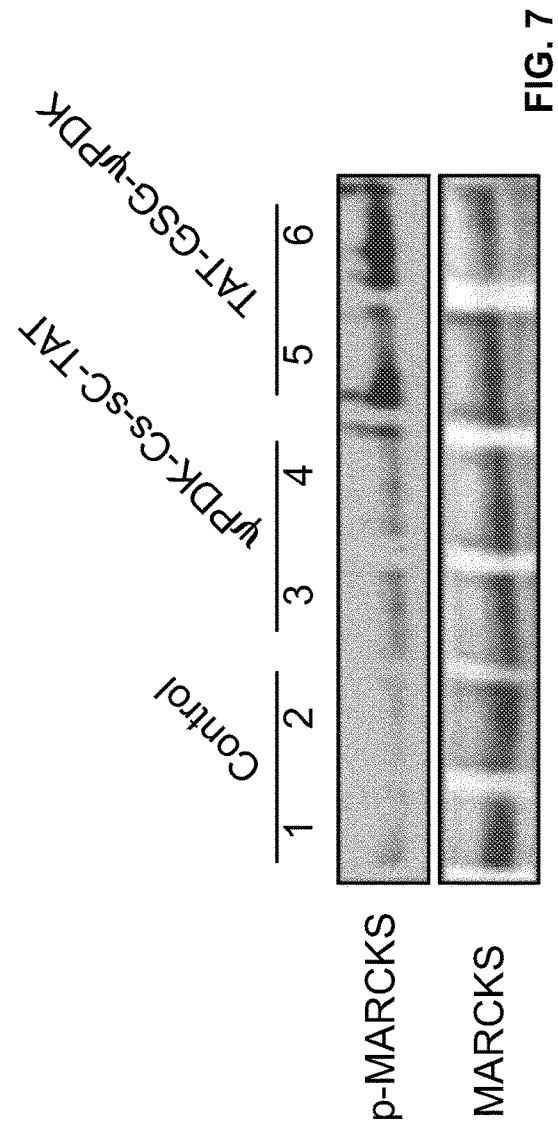
FIG. 6E shows a summary of the effect of control and experimental peptides on translocation of δPKC to the mitochondria and the effect on cardioprotection in an ex vivo model of I/R
FIG. 7 shows results of an assay to show phosphorylation of MARCKS by ΨPDK peptide attached to a carrier peptide via a disulfide bond (lanes 3-4) or via a peptide bond and spacer (lanes 5-6).

ΨPDK was also synthesized as a single polypeptide connected to TAT through an amide bond with a spacer of 3 amino acids (GSG) between the TAT on the N-terminus and the cargo on the C-terminus (referred to as ΨPDK-GSG-TAT (SEQ ID NO:41)). Interestingly, it was found that under these conditions, ΨPDK-GSG-TAT (SEQ ID NO:41) was a more effective δPKC regulator as compared to ΨPDK-Cs-sC-TAT (SEQ ID NO. 2 linked to SEQ ID NO. 33 via a disulfide bond, see FIG. 2A) when using MARCKS phosphorylation as an indicator of δPKC activity (FIG. 7). This might be due to improved delivery of ΨPDK-GSG-TAT (SEQ ID NO:41) into cells relative to ΨPDK-Cs-sC-TAT (SEQ ID NO. 2 linked to SEQ ID NO. 33 via a disulfide bond) releasable peptide, although this remains to be determined. Further, it was shown that the TAT-GSG-ΨPDK (the linear polypeptide, FIG. 2B, SEQ ID NO:42) was more cardioprotective: it greatly increased the protection from I/R injury from 45% protection (induced by the releasable peptide) to 73% protection (n=6).

It was surprisingly found that the PDK-related sequence in δPKC was identical (or almost identical) to that in PDK (FIG. 1B, D). This suggested a critical role for several or all the amino acids of the sequence ALSTE (SEQ ID NO:1). To begin determining the contribution of each of the amino acids on the effect of the peptide, Alanine scanning was used (Brunel et al., 2006, J. Virol., 80:1680-1687; Chen et al., J. Pep. Res., 2000, 56:147-156; Brems et al., 1992, Prot. Eng., 5:527-533) (substituting individual amino acid with an alanine). The resultant ΨPDK peptide analogs were then used in the same model of myocardial infarction, using CPK release and JNK phosphorylation as markers for cardiac injury. CPI release into the perfusates and pJNK in the hearts were determined after I/R in the presence of respective peptides and compared to the levels in hearts subjected to I/R in the presence of the control peptide. None of the peptides having a substitution had any significant biological activity (Table 1). In addition, although the S and T in ALSTER (SEQ ID NO:2) do not represent a consensus sequence for δPKC, it was next determined whether substituting S/T with phosphorylated S/T (denoted in Table 1 as S(p) and T(p), respectively) during synthesis alters the biological activity of the peptide. None of the phosphorylated peptides (p197, 198, 199) affected cardioprotection in the ex vivo I/R model (see Table 1). Therefore, only the ALSTER (SEQ ID NO:2) peptide was observed to exert cardio-protective effects as compared to the other peptide sequences described in Table 1, consistent with a role for each of the side groups of these amino acids in the interaction with δPKC.

TABLE 1

| Peptide | SEQ ID NO | Sequence | CPK (u/L) | p-JNK/total JNK |
|---------|-----------|----------|-----------|-----------------|
| ψPDK | 2 | ALSTER | 335 ± 520* | 0.4 ± 0.10* |
| p192 | 57 | AASTER | 1272 ± 172 | 0.7 ± 0.10 |
| p193 | 58 | ALATER | 1155 ± 299 | 0.7 ± 0.03 |
| p194 | 59 | ALSAER | 886 ± 211 | 0.6 ± 0.10 |
| p195 | 60 | ALSTAR | 913 ± 199 | 0.7 ± 0.10 |
| p196 | 61 | ALSTEA | 926 ± 265 | 0.9 ± 0.10* |
| p197 | 62 | ALST(p)ER | 803 ± 131 | 0.7 ± 0.10 |
| p198 | 63 | ALS(p)TER | 1169 ± 293 | 0.9 ± 0.10 |
| p199 | 64 | ALS(p)T(p)ER | 842 ± 258 | 0.6 ± 0.02 |
| control | — | | 964 ± 114 | 0.7 ± 0.02 |

*p < 0.01 vs. control
**T(p) refers to phosphorylated threonine; S(p) refers to phosphorylated serine.

It is claimed:

1. A therapeutic peptide having a sequence selected from SEQ ID NO: 41 and SEQ ID NO: 42.

2. The peptide of claim 1, wherein the peptide has the sequence of SEQ ID NO: 41.

3. The peptide of claim 1, wherein the peptide has the sequence of SEQ ID NO: 42.

4. A pharmaceutical composition comprising the therapeutic peptide according to claim 1 and a pharmaceutically acceptable excipient.

5. A method for treating a subject suffering from ischemic injury to cardiac tissue comprising administering to the subject the therapeutic peptide according to claim 1.

* * * * *

SEQUENCE LISTING

<160> NUMBER OF SEQ ID NOS: 55

<210> SEQ ID NO 1
<211> LENGTH: 5
<212> TYPE: PRT
<213> ORGANISM: Artificial sequence
<220> FEATURE:
<223> OTHER INFORMATION: Synthetic peptide

<400> SEQUENCE: 1

Ala Leu Ser Thr Glu
1               5

```
<210> SEQ ID NO 2
<211> LENGTH: 6
<212> TYPE: PRT
<213> ORGANISM: Artificial sequence
<220> FEATURE:
<223> OTHER INFORMATION: Synthetic peptide

<400> SEQUENCE: 2

Ala Leu Ser Thr Glu Arg
1               5

<210> SEQ ID NO 3
<211> LENGTH: 7
<212> TYPE: PRT
<213> ORGANISM: Artificial sequence
<220> FEATURE:
<223> OTHER INFORMATION: Synthetic peptide

<400> SEQUENCE: 3

Asp Leu Leu Pro Arg Gly Thr
1               5

<210> SEQ ID NO 4
<211> LENGTH: 6
<212> TYPE: PRT
<213> ORGANISM: Artificial sequence
<220> FEATURE:
<223> OTHER INFORMATION: Synthetic peptide

<400> SEQUENCE: 4

Gly Lys Thr Leu Val Gln
1               5

<210> SEQ ID NO 5
<211> LENGTH: 5
<212> TYPE: PRT
<213> ORGANISM: Artificial sequence
<220> FEATURE:
<223> OTHER INFORMATION: Synthetic peptide

<400> SEQUENCE: 5

Ala Leu Ser Thr Asp
1               5

<210> SEQ ID NO 6
<211> LENGTH: 6
<212> TYPE: PRT
<213> ORGANISM: Artificial sequence
<220> FEATURE:
<223> OTHER INFORMATION: Synthetic peptide

<400> SEQUENCE: 6

Ala Ile Ser Thr Glu Arg
1               5

<210> SEQ ID NO 7
<211> LENGTH: 6
<212> TYPE: PRT
<213> ORGANISM: Artificial sequence
<220> FEATURE:
<223> OTHER INFORMATION: Synthetic peptide

<400> SEQUENCE: 7

Ala Val Ser Thr Glu Arg
1               5
```

<210> SEQ ID NO 8
<211> LENGTH: 6
<212> TYPE: PRT
<213> ORGANISM: Artificial sequence
<220> FEATURE:
<223> OTHER INFORMATION: Synthetic peptide

<400> SEQUENCE: 8

Ala Leu Thr Thr Glu Arg
1               5

<210> SEQ ID NO 9
<211> LENGTH: 6
<212> TYPE: PRT
<213> ORGANISM: Artificial sequence
<220> FEATURE:
<223> OTHER INFORMATION: Synthetic peptide

<400> SEQUENCE: 9

Ala Thr Ser Ser Glu Arg
1               5

<210> SEQ ID NO 10
<211> LENGTH: 6
<212> TYPE: PRT
<213> ORGANISM: Artificial sequence
<220> FEATURE:
<223> OTHER INFORMATION: Synthetic peptide

<400> SEQUENCE: 10

Ala Leu Ser Thr Asp Arg
1               5

<210> SEQ ID NO 11
<211> LENGTH: 436
<212> TYPE: PRT
<213> ORGANISM: Homo sapiens

<400> SEQUENCE: 11

Met Arg Leu Ala Arg Leu Leu Arg Gly Ala Ala Leu Ala Gly Pro Gly
1               5                   10                  15

Pro Gly Leu Arg Ala Ala Gly Phe Ser Arg Ser Phe Ser Ser Asp Ser
                20                  25                  30

Gly Ser Ser Pro Ala Ser Glu Arg Gly Val Pro Gly Gln Val Asp Phe
            35                  40                  45

Tyr Ala Arg Phe Ser Pro Ser Pro Leu Ser Met Lys Gln Phe Leu Asp
        50                  55                  60

Phe Gly Ser Val Asn Ala Cys Glu Lys Thr Ser Phe Met Phe Leu Arg
65                  70                  75                  80

Gln Glu Leu Pro Val Arg Leu Ala Asn Ile Met Lys Glu Ile Ser Leu
                85                  90                  95

Leu Pro Asp Asn Leu Leu Arg Thr Pro Ser Val Gln Leu Val Gln Ser
                100                 105                 110

Trp Tyr Ile Gln Ser Leu Gln Glu Leu Leu Asp Phe Lys Asp Lys Ser
            115                 120                 125

Ala Glu Asp Ala Lys Ala Ile Tyr Asp Phe Thr Asp Thr Val Ile Arg
        130                 135                 140

Ile Arg Asn Arg His Asn Asp Val Ile Pro Thr Met Ala Gln Gly Val
145                 150                 155                 160

Ile Glu Tyr Lys Glu Ser Phe Gly Val Asp Pro Val Thr Ser Gln Asn
                165                 170                 175

Val Gln Tyr Phe Leu Asp Arg Phe Tyr Met Ser Arg Ile Ser Ile Arg
            180                 185                 190

Met Leu Leu Asn Gln His Ser Leu Phe Gly Gly Lys Gly Lys Gly
            195                 200                 205

Ser Pro Ser His Arg Lys His Ile Gly Ser Ile Asn Pro Asn Cys Asn
210                 215                 220

Val Leu Glu Val Ile Lys Asp Gly Tyr Glu Asn Ala Arg Arg Leu Cys
225                 230                 235                 240

Asp Leu Tyr Tyr Ile Asn Ser Pro Glu Leu Glu Leu Glu Leu Asn
                245                 250                 255

Ala Lys Ser Pro Gly Gln Pro Ile Gln Val Val Tyr Val Pro Ser His
            260                 265                 270

Leu Tyr His Met Val Phe Glu Leu Phe Lys Asn Ala Met Arg Ala Thr
            275                 280                 285

Met Glu His His Ala Asn Arg Gly Val Tyr Pro Pro Ile Gln Val His
            290                 295                 300

Val Thr Leu Gly Asn Glu Asp Leu Thr Val Lys Met Ser Asp Arg Gly
305                 310                 315                 320

Gly Gly Val Pro Leu Arg Lys Ile Asp Arg Leu Phe Asn Tyr Met Tyr
                325                 330                 335

Ser Thr Ala Pro Arg Pro Arg Val Glu Thr Ser Arg Ala Val Pro Leu
            340                 345                 350

Ala Gly Phe Gly Tyr Gly Leu Pro Ile Ser Arg Leu Tyr Ala Gln Tyr
            355                 360                 365

Phe Gln Gly Asp Leu Lys Leu Tyr Ser Leu Glu Gly Tyr Gly Thr Asp
370                 375                 380

Ala Val Ile Tyr Ile Lys Ala Leu Ser Thr Asp Ser Ile Glu Arg Leu
385                 390                 395                 400

Pro Val Tyr Asn Lys Ala Ala Trp Lys His Tyr Asn Thr Asn His Glu
                405                 410                 415

Ala Asp Asp Trp Cys Val Pro Ser Arg Glu Pro Lys Asp Met Thr Thr
            420                 425                 430

Phe Arg Ser Ala
        435

<210> SEQ ID NO 12
<211> LENGTH: 407
<212> TYPE: PRT
<213> ORGANISM: Homo sapiens

<400> SEQUENCE: 12

Met Arg Trp Val Trp Ala Leu Leu Lys Asn Ala Ser Leu Ala Gly Ala
1               5                   10                  15

Pro Lys Tyr Ile Glu His Phe Ser Lys Phe Ser Pro Ser Pro Leu Ser
                20                  25                  30

Met Lys Gln Phe Leu Asp Phe Gly Ser Ser Asn Ala Cys Glu Lys Thr
            35                  40                  45

Ser Phe Thr Phe Leu Arg Gln Glu Leu Pro Val Arg Leu Ala Asn Ile
        50                  55                  60

Met Lys Glu Ile Asn Leu Leu Pro Asp Arg Val Leu Ser Thr Pro Ser
65                  70                  75                  80

Val Gln Leu Val Gln Ser Trp Tyr Val Gln Ser Leu Leu Asp Ile Met
                85                  90                  95

Glu Phe Leu Asp Lys Asp Pro Glu Asp His Arg Thr Leu Ser Gln Phe

```
                100             105             110
Thr Asp Ala Leu Val Thr Ile Arg Asn Arg His Asn Asp Val Val Pro
            115                 120                 125
Thr Met Ala Gln Gly Val Leu Glu Tyr Lys Asp Thr Tyr Gly Asp Asp
            130                 135                 140
Pro Val Ser Asn Gln Asn Ile Gln Tyr Phe Leu Asp Arg Phe Tyr Leu
145                 150                 155                 160
Ser Arg Ile Ser Ile Arg Met Leu Ile Asn Gln His Thr Leu Ile Phe
                165                 170                 175
Asp Gly Ser Thr Asn Pro Ala His Pro Lys His Ile Gly Ser Ile Asp
                180                 185                 190
Pro Asn Cys Asn Val Ser Glu Val Val Lys Asp Ala Tyr Asp Met Ala
                195                 200                 205
Lys Leu Leu Cys Asp Lys Tyr Tyr Met Ala Ser Pro Asp Leu Glu Ile
            210                 215                 220
Gln Glu Ile Asn Ala Ala Asn Ser Lys Gln Pro Ile His Met Val Tyr
225                 230                 235                 240
Val Pro Ser His Leu Tyr His Met Leu Phe Glu Leu Phe Lys Asn Ala
                245                 250                 255
Met Arg Ala Thr Val Glu Ser His Glu Ser Ser Leu Ile Leu Pro Pro
                260                 265                 270
Ile Lys Val Met Val Ala Leu Gly Glu Glu Asp Leu Ser Ile Lys Met
                275                 280                 285
Ser Asp Arg Gly Gly Gly Val Pro Leu Arg Lys Ile Glu Arg Leu Phe
            290                 295                 300
Ser Tyr Met Tyr Ser Thr Ala Pro Thr Pro Gln Pro Gly Thr Gly Gly
305                 310                 315                 320
Thr Pro Leu Ala Gly Phe Gly Tyr Gly Leu Pro Ile Ser Arg Leu Tyr
                325                 330                 335
Ala Lys Tyr Phe Gln Gly Asp Leu Gln Leu Phe Ser Met Glu Gly Phe
                340                 345                 350
Gly Thr Asp Ala Val Ile Tyr Leu Lys Ala Leu Ser Thr Asp Ser Val
            355                 360                 365
Glu Arg Leu Pro Val Tyr Asn Lys Ser Ala Trp Arg His Tyr Gln Thr
            370                 375                 380
Ile Gln Glu Ala Gly Asp Trp Cys Val Pro Ser Thr Glu Pro Lys Asn
385                 390                 395                 400
Thr Ser Thr Tyr Arg Val Ser
                405

<210> SEQ ID NO 13
<211> LENGTH: 415
<212> TYPE: PRT
<213> ORGANISM: Homo sapiens

<400> SEQUENCE: 13

Met Arg Leu Phe Arg Trp Leu Leu Lys Gln Pro Val Pro Lys Gln Ile
1               5                   10                  15
Glu Arg Tyr Ser Arg Phe Ser Pro Ser Pro Leu Ser Ile Lys Gln Phe
            20                  25                  30
Leu Asp Phe Gly Arg Asp Asn Ala Cys Glu Lys Thr Ser Tyr Met Phe
            35                  40                  45
Leu Arg Lys Glu Leu Pro Val Arg Leu Ala Asn Thr Met Arg Glu Val
        50                  55                  60
```

Asn Leu Leu Pro Asp Asn Leu Leu Asn Arg Pro Ser Val Gly Leu Val
 65                  70                  75                  80

Gln Ser Trp Tyr Met Gln Ser Phe Leu Glu Leu Leu Glu Tyr Glu Asn
                 85                  90                  95

Lys Ser Pro Glu Asp Pro Gln Val Leu Asp Asn Phe Leu Gln Val Leu
            100                 105                 110

Ile Lys Val Arg Asn Arg His Asn Asp Val Val Pro Thr Met Ala Gln
        115                 120                 125

Gly Val Ile Glu Tyr Lys Glu Lys Phe Gly Phe Asp Pro Phe Ile Ser
    130                 135                 140

Thr Asn Ile Gln Tyr Phe Leu Asp Arg Phe Tyr Thr Asn Arg Ile Ser
145                 150                 155                 160

Phe Arg Met Leu Ile Asn Gln His Thr Leu Leu Phe Gly Gly Asp Thr
                165                 170                 175

Asn Pro Val His Pro Lys His Ile Gly Ser Ile Asp Pro Thr Cys Asn
            180                 185                 190

Val Ala Asp Val Val Lys Asp Ala Tyr Glu Thr Ala Lys Met Leu Cys
        195                 200                 205

Glu Gln Tyr Tyr Leu Val Ala Pro Glu Leu Glu Val Glu Glu Phe Asn
    210                 215                 220

Ala Lys Ala Pro Asp Lys Pro Ile Gln Val Val Tyr Val Pro Ser His
225                 230                 235                 240

Leu Phe His Met Leu Phe Glu Leu Phe Lys Asn Ser Met Arg Ala Thr
                245                 250                 255

Val Glu Leu Tyr Glu Asp Arg Lys Glu Gly Tyr Pro Ala Val Lys Thr
            260                 265                 270

Leu Val Thr Leu Gly Lys Glu Asp Leu Ser Ile Lys Ile Ser Asp Leu
        275                 280                 285

Gly Gly Gly Val Pro Leu Arg Lys Ile Asp Arg Leu Phe Asn Tyr Met
    290                 295                 300

Tyr Ser Thr Ala Pro Arg Pro Ser Leu Glu Pro Thr Arg Ala Ala Pro
305                 310                 315                 320

Leu Ala Gly Phe Gly Tyr Gly Leu Pro Ile Ser Arg Leu Tyr Ala Arg
                325                 330                 335

Tyr Phe Gln Gly Asp Leu Lys Leu Tyr Ser Met Glu Gly Val Gly Thr
            340                 345                 350

Asp Ala Val Ile Tyr Leu Lys Ala Leu Ser Ser Glu Ser Phe Glu Arg
        355                 360                 365

Leu Pro Val Phe Asn Lys Ser Ala Trp Arg His Tyr Lys Thr Thr Pro
    370                 375                 380

Glu Ala Asp Asp Trp Ser Asn Pro Ser Ser Glu Pro Arg Asp Ala Ser
385                 390                 395                 400

Lys Tyr Lys Ala Lys Gln Asp Lys Ile Lys Thr Asn Arg Thr Phe
                405                 410                 415

<210> SEQ ID NO 14
<211> LENGTH: 411
<212> TYPE: PRT
<213> ORGANISM: Homo sapiens

<400> SEQUENCE: 14

Met Lys Ala Ala Arg Phe Val Leu Arg Ser Ala Gly Ser Leu Asn Gly
1               5                   10                  15

Ala Gly Leu Val Pro Arg Glu Val Glu His Phe Ser Arg Tyr Ser Pro
            20                  25                  30

Ser Pro Leu Ser Met Lys Gln Leu Leu Asp Phe Gly Ser Glu Asn Ala
              35                  40                  45

Cys Glu Arg Thr Ser Phe Ala Phe Leu Arg Gln Glu Leu Pro Val Arg
 50                  55                  60

Leu Ala Asn Ile Leu Lys Glu Ile Asp Ile Leu Pro Thr Gln Leu Val
 65                  70                  75                  80

Asn Thr Ser Ser Val Gln Leu Val Lys Ser Trp Tyr Ile Gln Ser Leu
                 85                  90                  95

Met Asp Leu Val Glu Phe His Glu Lys Ser Pro Asp Asp Gln Lys Ala
                100                 105                 110

Leu Ser Asp Phe Val Asp Thr Leu Ile Lys Val Arg Asn Arg His His
                115                 120                 125

Asn Val Val Pro Thr Met Ala Gln Gly Ile Ile Glu Tyr Lys Asp Ala
130                 135                 140

Cys Thr Val Asp Pro Val Thr Asn Gln Asn Leu Gln Tyr Phe Leu Asp
145                 150                 155                 160

Arg Phe Tyr Met Asn Arg Ile Ser Thr Arg Met Leu Met Asn Gln His
                165                 170                 175

Ile Leu Ile Phe Ser Asp Ser Gln Thr Gly Asn Pro Ser His Ile Gly
                180                 185                 190

Ser Ile Asp Pro Asn Cys Asp Val Val Ala Val Val Gln Asp Ala Phe
                195                 200                 205

Glu Cys Ser Arg Met Leu Cys Asp Gln Tyr Tyr Leu Ser Ser Pro Glu
                210                 215                 220

Leu Lys Leu Thr Gln Val Asn Gly Lys Phe Pro Asp Gln Pro Ile His
225                 230                 235                 240

Ile Val Tyr Val Pro Ser His Leu His His Met Leu Phe Glu Leu Phe
                245                 250                 255

Lys Asn Ala Met Arg Ala Thr Val Glu His Gln Glu Asn Gln Pro Ser
                260                 265                 270

Leu Thr Pro Ile Glu Val Ile Val Leu Gly Lys Glu Asp Leu Thr
                275                 280                 285

Ile Lys Ile Ser Asp Arg Gly Gly Gly Val Pro Leu Arg Ile Ile Asp
                290                 295                 300

Arg Leu Phe Ser Tyr Thr Tyr Ser Thr Ala Pro Thr Pro Val Met Asp
305                 310                 315                 320

Asn Ser Arg Asn Ala Pro Leu Ala Gly Phe Gly Tyr Gly Leu Pro Ile
                325                 330                 335

Ser Arg Leu Tyr Ala Lys Tyr Phe Gln Gly Asp Leu Asn Leu Tyr Ser
                340                 345                 350

Leu Ser Gly Tyr Gly Thr Asp Ala Ile Ile Tyr Leu Lys Ala Leu Ser
                355                 360                 365

Ser Glu Ser Ile Glu Lys Leu Pro Val Phe Asn Lys Ser Ala Phe Lys
370                 375                 380

His Tyr Gln Met Ser Ser Glu Ala Asp Asp Trp Cys Ile Pro Ser Arg
385                 390                 395                 400

Glu Pro Lys Asn Leu Ala Lys Glu Val Ala Met
                405                 410

<210> SEQ ID NO 15
<211> LENGTH: 16
<212> TYPE: PRT
<213> ORGANISM: Artificial sequence
<220> FEATURE:

<223> OTHER INFORMATION: Synthetic peptide

<400> SEQUENCE: 15

Lys Met Lys Glu Ala Leu Ser Thr Glu Arg Gly Lys Thr Leu Val Gln
1               5                   10                  15

<210> SEQ ID NO 16
<211> LENGTH: 16
<212> TYPE: PRT
<213> ORGANISM: Artificial sequence
<220> FEATURE:
<223> OTHER INFORMATION: Synthetic peptide

<400> SEQUENCE: 16

Ile Tyr Leu Lys Ala Leu Ser Thr Asp Ser Val Glu Arg Leu Pro Val
1               5                   10                  15

<210> SEQ ID NO 17
<211> LENGTH: 25
<212> TYPE: PRT
<213> ORGANISM: Artificial sequence
<220> FEATURE:
<223> OTHER INFORMATION: Synthetic peptide

<400> SEQUENCE: 17

Pro Phe Cys Ala Val Lys Met Lys Glu Ala Leu Ser Thr Glu Arg Gly
1               5                   10                  15

Lys Thr Leu Val Gln Lys Lys Pro Thr
            20                  25

<210> SEQ ID NO 18
<211> LENGTH: 25
<212> TYPE: PRT
<213> ORGANISM: Artificial sequence
<220> FEATURE:
<223> OTHER INFORMATION: Synthetic peptide

<400> SEQUENCE: 18

Pro Phe Cys Ala Val Lys Met Lys Glu Ala Leu Ser Thr Glu Arg Gly
1               5                   10                  15

Lys Thr Leu Val Gln Lys Lys Pro Thr
            20                  25

<210> SEQ ID NO 19
<211> LENGTH: 25
<212> TYPE: PRT
<213> ORGANISM: Artificial sequence
<220> FEATURE:
<223> OTHER INFORMATION: Synthetic peptide

<400> SEQUENCE: 19

Pro Phe Cys Ala Val Lys Met Lys Glu Ala Leu Thr Thr Asp Arg Gly
1               5                   10                  15

Lys Thr Leu Val Gln Lys Lys Pro Thr
            20                  25

<210> SEQ ID NO 20
<211> LENGTH: 25
<212> TYPE: PRT
<213> ORGANISM: Artificial sequence
<220> FEATURE:
<223> OTHER INFORMATION: Synthetic peptide

<400> SEQUENCE: 20

Pro Phe Cys Ala Ile Lys Met Lys Glu Ala Leu Thr Thr Glu Arg Gly

```
1               5                   10                  15
Lys Thr Leu Ile Gln Arg Lys Pro Thr
            20                  25

<210> SEQ ID NO 21
<211> LENGTH: 25
<212> TYPE: PRT
<213> ORGANISM: Artificial sequence
<220> FEATURE:
<223> OTHER INFORMATION: Synthetic peptide

<400> SEQUENCE: 21

Pro Phe Cys Ala Val Lys Met Lys Glu Ala Leu Ser Thr Glu Arg Gly
1               5                   10                  15

Lys Thr Leu Val Gln Lys Lys Pro Thr
            20                  25

<210> SEQ ID NO 22
<211> LENGTH: 22
<212> TYPE: PRT
<213> ORGANISM: Artificial sequence
<220> FEATURE:
<223> OTHER INFORMATION: Synthetic peptide

<400> SEQUENCE: 22

Phe Ser Met Glu Gly Phe Gly Thr Asp Ala Val Ile Tyr Leu Lys Ala
1               5                   10                  15

Leu Ser Thr Asp Ser Val
            20

<210> SEQ ID NO 23
<211> LENGTH: 22
<212> TYPE: PRT
<213> ORGANISM: Artificial sequence
<220> FEATURE:
<223> OTHER INFORMATION: Synthetic peptide

<400> SEQUENCE: 23

Phe Ser Met Glu Gly Phe Gly Thr Asp Ala Val Ile Tyr Leu Lys Ala
1               5                   10                  15

Leu Ser Thr Asp Ser Val
            20

<210> SEQ ID NO 24
<211> LENGTH: 22
<212> TYPE: PRT
<213> ORGANISM: Artificial sequence
<220> FEATURE:
<223> OTHER INFORMATION: Synthetic peptide

<400> SEQUENCE: 24

Phe Ser Met Glu Gly Phe Gly Thr Asp Ala Val Ile Tyr Leu Lys Ala
1               5                   10                  15

Leu Ser Thr Asp Ser Val
            20

<210> SEQ ID NO 25
<211> LENGTH: 22
<212> TYPE: PRT
<213> ORGANISM: Artificial sequence
<220> FEATURE:
<223> OTHER INFORMATION: Synthetic peptide

<400> SEQUENCE: 25
```

Tyr Ser Leu Glu Gly Tyr Gly Thr Asp Ala Val Ile Tyr Ile Lys Ala
1               5                   10                  15

Leu Ser Thr Glu Ser Ile
            20

<210> SEQ ID NO 26
<211> LENGTH: 22
<212> TYPE: PRT
<213> ORGANISM: Artificial sequence
<220> FEATURE:
<223> OTHER INFORMATION: Synthetic peptide

<400> SEQUENCE: 26

Tyr Pro Met Glu Gly Tyr Gly Thr Asp Ala Val Ile Gln Leu Lys Ala
1               5                   10                  15

Leu Ser Thr Asp Ser Val
            20

<210> SEQ ID NO 27
<211> LENGTH: 22
<212> TYPE: PRT
<213> ORGANISM: Artificial sequence
<220> FEATURE:
<223> OTHER INFORMATION: Synthetic peptide

<400> SEQUENCE: 27

Leu Ser Cys Glu Gly Phe Gly Thr Asp Ala Ile Ile Tyr Leu Lys Ala
1               5                   10                  15

Leu Ser Asp Glu Ala Asn
            20

<210> SEQ ID NO 28
<211> LENGTH: 22
<212> TYPE: PRT
<213> ORGANISM: Artificial sequence
<220> FEATURE:
<223> OTHER INFORMATION: Synthetic peptide

<400> SEQUENCE: 28

Val Ser Met Glu Gly Tyr Gly Thr Asp Ala Met Ile Phe Leu Lys Ala
1               5                   10                  15

Ile Pro Val Glu Ala Ser
            20

<210> SEQ ID NO 29
<211> LENGTH: 22
<212> TYPE: PRT
<213> ORGANISM: Artificial sequence
<220> FEATURE:
<223> OTHER INFORMATION: Synthetic peptide

<400> SEQUENCE: 29

Gln Ser Leu Leu Gly Trp Gly Thr Asp Val Tyr Ile Lys Leu Lys Gly
1               5                   10                  15

Pro Ser Lys Thr Ala Leu
            20

<210> SEQ ID NO 30
<211> LENGTH: 140
<212> TYPE: PRT
<213> ORGANISM: Homo sapiens

<400> SEQUENCE: 30

Met Val Val Phe Asn Gly Leu Leu Lys Ile Lys Ile Cys Glu Ala Val

-continued

```
               1               5                  10                 15
            Ser Leu Lys Pro Thr Ala Trp Ser Leu Arg His Ala Val Gly Pro Arg
                            20                 25                 30

Pro Gln Thr Phe Leu Leu Asp Pro Tyr Ile Ala Leu Asn Val Asp Asp
                            35                 40                 45

Ser Arg Ile Gly Gln Thr Ala Thr Lys Gln Lys Thr Asn Ser Pro Ala
                50                         55                 60

Trp His Asp Glu Phe Val Ile Asp Val Cys Asn Gly Arg Lys Ile Glu
             65                 70                 75                 80

Leu Ala Val Phe His Asp Ala Pro Ile Gly Tyr Asp Asp Phe Val Ala
                                85                 90                 95

Asn Cys Thr Ile Gln Phe Glu Glu Leu Leu Gln Asn Gly Ser Arg His
                            100                105                110

Phe Glu Asp Trp Ile Asp Leu Glu Pro Glu Gly Lys Val Tyr Val Ile
                            115                120                125

Ile Asp Leu Ser Gly Ser Ser Gly Glu Ala Pro Lys
                            130                135                140
```

<210> SEQ ID NO 31
<211> LENGTH: 129
<212> TYPE: PRT
<213> ORGANISM: Homo sapiens

<400> SEQUENCE: 31

```
            Met Ala Pro Phe Leu Arg Ile Ser Phe Asn Ser Tyr Glu Leu Gly Ser
             1               5                  10                 15

Leu Gln Ala Glu Asp Glu Ala Asn Gln Pro Phe Cys Ala Val Lys Met
                            20                 25                 30

Lys Glu Ala Leu Ser Thr Glu Arg Gly Lys Thr Leu Val Gln Lys Lys
                            35                 40                 45

Pro Thr Met Tyr Pro Glu Trp Lys Ser Thr Phe Asp Ala His Ile Tyr
                            50                 55                 60

Glu Gly Arg Val Ile Gln Ile Val Leu Met Arg Ala Ala Glu Glu Pro
             65                 70                 75                 80

Met Ser Glu Val Thr Val Gly Val Ser Val Leu Ala Glu Arg Cys Lys
                            85                 90                 95

Lys Asn Asn Gly Lys Ala Glu Phe Trp Leu Asp Leu Gln Pro Gln Ala
                            100                105                110

Lys Val Leu Met Ser Val Gln Tyr Phe Leu Glu Asp Val Asp Cys Lys
                            115                120                125

Gln
```

<210> SEQ ID NO 32
<211> LENGTH: 130
<212> TYPE: PRT
<213> ORGANISM: Homo sapiens

<400> SEQUENCE: 32

```
            Met Ser Pro Phe Leu Arg Ile Gly Leu Ser Asn Phe Asp Cys Gly Ser
             1               5                  10                 15

Cys Gln Ser Cys Gln Gly Glu Ala Val Asn Pro Tyr Cys Ala Val Leu
                            20                 25                 30

Val Lys Glu Tyr Val Glu Ser Glu Asn Gly Gln Met Tyr Ile Gln Lys
                            35                 40                 45

Lys Pro Thr Met Tyr Pro Pro Trp Asp Ser Thr Phe Asp Ala His Ile
                            50                 55                 60
```

```
Asn Lys Gly Arg Val Met Gln Ile Ile Val Lys Gly Lys Asn Val Asp
 65                  70                  75                  80

Leu Ile Ser Glu Thr Thr Val Glu Leu Tyr Ser Leu Ala Glu Arg Cys
             85                  90                  95

Arg Lys Asn Asn Gly Lys Thr Glu Ile Trp Leu Glu Leu Lys Pro Gln
        100                 105                 110

Gly Arg Met Leu Met Asn Ala Arg Tyr Phe Leu Glu Met Ser Asp Thr
        115                 120                 125

Lys Asp
    130

<210> SEQ ID NO 33
<211> LENGTH: 11
<212> TYPE: PRT
<213> ORGANISM: Artificial sequence
<220> FEATURE:
<223> OTHER INFORMATION: Synthetic peptide

<400> SEQUENCE: 33

Tyr Gly Arg Lys Lys Arg Arg Gln Arg Arg Arg
1               5                   10

<210> SEQ ID NO 34
<211> LENGTH: 6
<212> TYPE: PRT
<213> ORGANISM: Artificial sequence
<220> FEATURE:
<223> OTHER INFORMATION: Synthetic peptide

<400> SEQUENCE: 34

Gly Lys Thr Leu Val Gln
1               5

<210> SEQ ID NO 35
<211> LENGTH: 5
<212> TYPE: PRT
<213> ORGANISM: Artificial sequence
<220> FEATURE:
<223> OTHER INFORMATION: Synthetic peptide

<400> SEQUENCE: 35

Ala Leu Ser Thr Asp
1               5

<210> SEQ ID NO 36
<211> LENGTH: 6
<212> TYPE: PRT
<213> ORGANISM: Artificial sequence
<220> FEATURE:
<223> OTHER INFORMATION: Synthetic peptide

<400> SEQUENCE: 36

Ala Ile Ser Thr Glu Arg
1               5

<210> SEQ ID NO 37
<211> LENGTH: 6
<212> TYPE: PRT
<213> ORGANISM: Artificial sequence
<220> FEATURE:
<223> OTHER INFORMATION: Synthetic peptide

<400> SEQUENCE: 37

Ala Val Ser Thr Glu Arg
```

```
<210> SEQ ID NO 38
<211> LENGTH: 6
<212> TYPE: PRT
<213> ORGANISM: Artificial sequence
<220> FEATURE:
<223> OTHER INFORMATION: Synthetic peptide

<400> SEQUENCE: 38

Ala Leu Thr Thr Glu Arg
1               5

<210> SEQ ID NO 39
<211> LENGTH: 6
<212> TYPE: PRT
<213> ORGANISM: Artificial sequence
<220> FEATURE:
<223> OTHER INFORMATION: Synthetic peptide

<400> SEQUENCE: 39

Ala Thr Ser Ser Glu Arg
1               5

<210> SEQ ID NO 40
<211> LENGTH: 6
<212> TYPE: PRT
<213> ORGANISM: Artificial sequence
<220> FEATURE:
<223> OTHER INFORMATION: Synthetic peptide

<400> SEQUENCE: 40

Ala Leu Ser Thr Asp Arg
1               5

<210> SEQ ID NO 41
<211> LENGTH: 20
<212> TYPE: PRT
<213> ORGANISM: Artificial sequence
<220> FEATURE:
<223> OTHER INFORMATION: Synthetic peptide

<400> SEQUENCE: 41

Ala Leu Ser Thr Glu Arg Gly Ser Gly Tyr Gly Arg Lys Lys Arg Arg
1               5                   10                  15

Gln Arg Arg Arg
            20

<210> SEQ ID NO 42
<211> LENGTH: 20
<212> TYPE: PRT
<213> ORGANISM: Artificial sequence
<220> FEATURE:
<223> OTHER INFORMATION: Synthetic peptide

<400> SEQUENCE: 42

Tyr Gly Arg Lys Lys Arg Arg Gln Arg Arg Arg Gly Ser Gly Ala Leu
1               5                   10                  15

Ser Thr Glu Arg
            20

<210> SEQ ID NO 43
<211> LENGTH: 11
<212> TYPE: PRT
<213> ORGANISM: Artificial sequence
<220> FEATURE:
```

<223> OTHER INFORMATION: Synthetic peptide

<400> SEQUENCE: 43

Ala Leu Ser Thr Glu Arg Gly Lys Thr Leu Val
1               5                   10

<210> SEQ ID NO 44
<211> LENGTH: 11
<212> TYPE: PRT
<213> ORGANISM: Artificial sequence
<220> FEATURE:
<223> OTHER INFORMATION: Synthetic peptide

<400> SEQUENCE: 44

Ala Leu Ser Thr Asp Arg Gly Lys Thr Leu Val
1               5                   10

<210> SEQ ID NO 45
<211> LENGTH: 11
<212> TYPE: PRT
<213> ORGANISM: Artificial sequence
<220> FEATURE:
<223> OTHER INFORMATION: Synthetic peptide

<400> SEQUENCE: 45

Ala Leu Thr Thr Asp Arg Gly Lys Thr Leu Val
1               5                   10

<210> SEQ ID NO 46
<211> LENGTH: 11
<212> TYPE: PRT
<213> ORGANISM: Artificial sequence
<220> FEATURE:
<223> OTHER INFORMATION: Synthetic peptide

<400> SEQUENCE: 46

Ala Leu Thr Thr Asp Arg Gly Arg Thr Leu Val
1               5                   10

<210> SEQ ID NO 47
<211> LENGTH: 11
<212> TYPE: PRT
<213> ORGANISM: Artificial sequence
<220> FEATURE:
<223> OTHER INFORMATION: Synthetic peptide

<400> SEQUENCE: 47

Ala Leu Thr Thr Asp Arg Gly Lys Ser Leu Val
1               5                   10

<210> SEQ ID NO 48
<211> LENGTH: 11
<212> TYPE: PRT
<213> ORGANISM: Artificial sequence
<220> FEATURE:
<223> OTHER INFORMATION: Synthetic peptide

<400> SEQUENCE: 48

Ala Leu Thr Ser Asp Arg Gly Lys Thr Leu Val
1               5                   10

<210> SEQ ID NO 49
<211> LENGTH: 11
<212> TYPE: PRT
<213> ORGANISM: Artificial sequence
<220> FEATURE:
<223> OTHER INFORMATION: Synthetic peptide

```
<400> SEQUENCE: 49

Ala Leu Thr Thr Asp Arg Pro Lys Thr Leu Val
1               5                   10

<210> SEQ ID NO 50
<211> LENGTH: 10
<212> TYPE: PRT
<213> ORGANISM: Artificial sequence
<220> FEATURE:
<223> OTHER INFORMATION: Synthetic peptide

<400> SEQUENCE: 50

Ala Leu Thr Thr Asp Lys Gly Lys Thr Leu
1               5                   10

<210> SEQ ID NO 51
<211> LENGTH: 10
<212> TYPE: PRT
<213> ORGANISM: Artificial sequence
<220> FEATURE:
<223> OTHER INFORMATION: Synthetic peptide

<400> SEQUENCE: 51

Ala Leu Thr Thr Asp Arg Gly Lys Leu Val
1               5                   10

<210> SEQ ID NO 52
<211> LENGTH: 12
<212> TYPE: PRT
<213> ORGANISM: Artificial sequence
<220> FEATURE:
<223> OTHER INFORMATION: Synthetic peptide

<400> SEQUENCE: 52

Tyr Gly Arg Lys Lys Arg Arg Gln Arg Arg Cys
1               5                   10

<210> SEQ ID NO 53
<211> LENGTH: 7
<212> TYPE: PRT
<213> ORGANISM: Artificial sequence
<220> FEATURE:
<223> OTHER INFORMATION: Synthetic peptide

<400> SEQUENCE: 53

Ala Leu Ser Thr Glu Arg Cys
1               5

<210> SEQ ID NO 54
<211> LENGTH: 12
<212> TYPE: PRT
<213> ORGANISM: Artificial sequence
<220> FEATURE:
<223> OTHER INFORMATION: Synthetic peptide

<400> SEQUENCE: 54

Cys Tyr Gly Arg Lys Lys Arg Arg Gln Arg Arg Arg
1               5                   10

<210> SEQ ID NO 55
<211> LENGTH: 7
<212> TYPE: PRT
<213> ORGANISM: Artificial sequence
<220> FEATURE:
<223> OTHER INFORMATION: Synthetic peptide
```

```
<400> SEQUENCE: 55

Cys Ala Leu Ser Thr Glu Arg
1               5
```